US011166652B2

(12) United States Patent
Cuccia et al.

(10) Patent No.: US 11,166,652 B2
(45) Date of Patent: Nov. 9, 2021

(54) METHOD AND APPARATUS FOR ASSESSING TISSUE VASCULAR HEALTH

(71) Applicant: MODULATED IMAGING, INC., Irvine, CA (US)

(72) Inventors: David Cuccia, Costa Mesa, CA (US); Amaan Mazhar, Corona Del Mar, CA (US)

(73) Assignee: MODULATED IMAGING, INC., Irvine, CA (US)

( * ) Notice: Subject to any disclaimer, the term of this patent is extended or adjusted under 35 U.S.C. 154(b) by 0 days.

(21) Appl. No.: 15/431,627

(22) Filed: Feb. 13, 2017

(65) Prior Publication Data

US 2017/0319115 A1    Nov. 9, 2017

Related U.S. Application Data

(60) Provisional application No. 62/294,919, filed on Feb. 12, 2016.

(51) Int. Cl.

| | |
|---|---|
| *A61B 5/1455* | (2006.01) |
| *A61B 5/00* | (2006.01) |
| *A61B 5/026* | (2006.01) |
| *A61B 5/02* | (2006.01) |
| *A61B 5/145* | (2006.01) |

(52) U.S. Cl.
CPC ........ *A61B 5/14551* (2013.01); *A61B 5/0004* (2013.01); *A61B 5/0077* (2013.01); *A61B 5/02* (2013.01); *A61B 5/026* (2013.01); *A61B 5/1455* (2013.01); *A61B 5/14546* (2013.01); *A61B 5/489* (2013.01); *A61B 5/7271* (2013.01); *A61B 5/7435* (2013.01)

(58) Field of Classification Search
CPC . A61B 5/14551; A61B 5/7435; A61B 5/0004; A61B 5/14546; A61B 5/7271
See application file for complete search history.

(56) References Cited

U.S. PATENT DOCUMENTS

| | | | |
|---|---|---|---|
| 6,958,815 B2 * | 10/2005 | Bevilacqua | ............ G01N 21/49 356/445 |
| 9,220,412 B2 | 12/2015 | Cuccia | |
| 2003/0139667 A1 | 7/2003 | Hewko et al. | |

(Continued)

OTHER PUBLICATIONS

Lin et al., Spatial Frequency Domain Imaging of Intrinsic Optical Property Contrast in a Mouse Model of Alzheimer's Disease, Ann Biomed Eng. Apr. 2011; 39(4): 1349-1357, Published online Feb. 19, 2011.*

(Continued)

*Primary Examiner* — Bo Joseph Peng
(74) *Attorney, Agent, or Firm* — One LLP

(57) ABSTRACT

Systems and methods directed to the assessment of tissue vascular health. An optical measurement device includes a light source with one or more wavelengths, configured to illuminate an area of tissue, a detector configured to capture the light reflecting from the tissue at the one or more illumination wavelengths, a processor configured to compute, based on the detected signal, one or more estimates of tissue vascular health, and a display or communication device (e.g., electronic data transfer) configured to store or report the tissue vascular health.

6 Claims, 27 Drawing Sheets

(56) References Cited

U.S. PATENT DOCUMENTS

| | | | |
|---|---|---|---|
| 2003/0184757 A1* | 10/2003 | Bevilacqua | G01N 21/49 |
| | | | 356/445 |
| 2005/0273011 A1* | 12/2005 | Hattery | A61B 5/0059 |
| | | | 600/476 |
| 2009/0118622 A1* | 5/2009 | Durkin | A61B 5/0073 |
| | | | 600/473 |
| 2010/0210931 A1 | 8/2010 | Cuccia et al. | |
| 2011/0230715 A1* | 9/2011 | Saito | G06T 7/0012 |
| | | | 600/109 |
| 2012/0283530 A1 | 11/2012 | Maynard et al. | |
| 2013/0274612 A1 | 10/2013 | Cuccia | |
| 2014/0128744 A1 | 5/2014 | Cuccia et al. | |
| 2014/0194749 A1 | 7/2014 | Fixler et al. | |
| 2014/0213910 A1* | 7/2014 | Durkin | G06T 7/0012 |
| | | | 600/477 |
| 2015/0133754 A1 | 5/2015 | Freeman et al. | |

OTHER PUBLICATIONS

WO, PCT/US2017/017727 ISR and Written Opinion, dated May 10, 2017.

Liu, X. C., et al., "CCD/CMOS Hybrid FPA for Low Light Level Imaging", International Society for Optics and Photonics, 2005, pp. 1-9.

EP, 17750984.1 Supplementary Search Report, dated Aug. 13, 2019.

\* cited by examiner

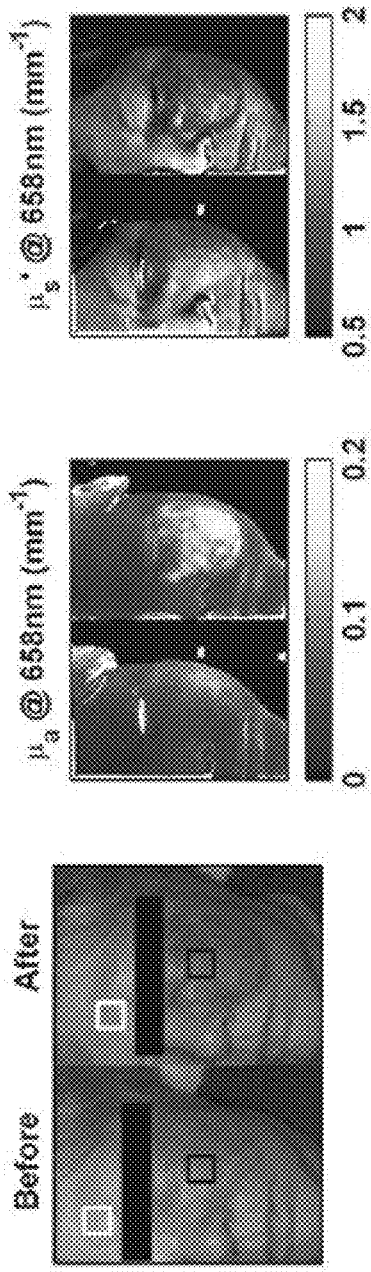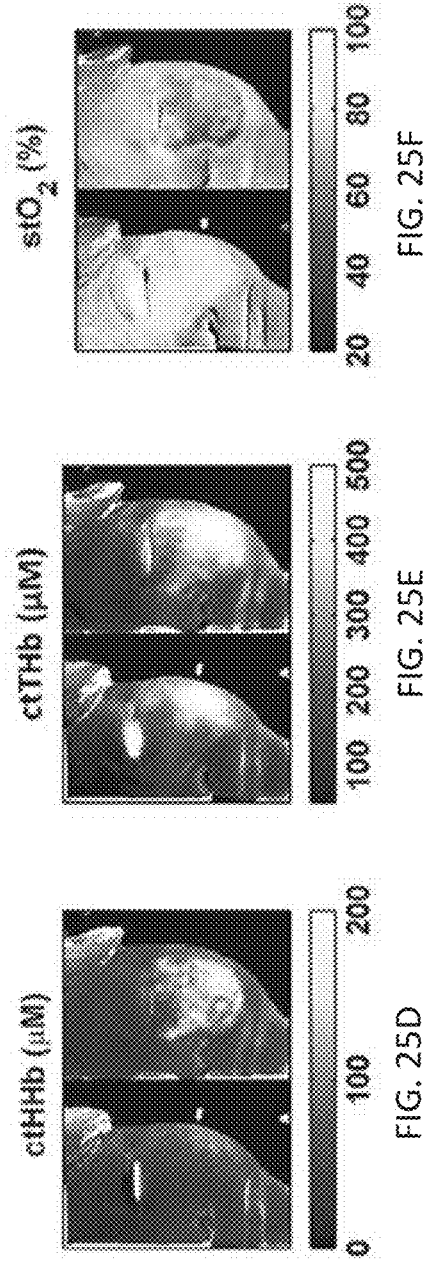
(Before (left) and after (right) port wine stain pulsed dye laser therapy (a) Color images (b)-(f) chromophore maps from SFDI measurements)

METHOD AND APPARATUS FOR ASSESSING TISSUE VASCULAR HEALTH

CROSS REFERENCE TO RELATED APPLICATIONS

The present application claims the benefit of priority to U.S. Provisional Application No. 62/294,919, titled "METHOD AND APPARATUS FOR ASSESSING TISSUE VASCULAR HEALTH" filed Feb. 12, 2016, the contents of which are incorporated herein by reference in their entirety.

FIELD

The embodiments described herein relate generally to optical measurement of tissue media, and, more particularly, to systems and methods directed to the assessment of tissue vascular health.

BACKGROUND

Improvement is needed in the management of acute and chronic wounds including diabetic foot ulcers, decubitus ulcers, and burns. Most complications in wounds result from a lack of proper blood supply and drainage to local tissues (capillary bed) leading to tissue necrosis and eventual death. For example, diabetic and decubitus ulcers (pressure sores) are cutaneous wounds that will not heal under normal circumstances due to hypoxic conditions from poor circulation. In every wound case, throughout the course of its treatment, the consideration for the health of the surrounding tissue remains the same: "Is the tissue at the area of concern receiving sufficient oxygen rich blood to promote a wound healing response?" The most accepted method for answering this question remains visual clinical impression which is highly subjective diagnosis and can vary between health care providers causing a disparity in effective treatment plans.

Diabetes mellitus affected 382 million adults worldwide in 2013 and is expected to increase in prevalence to 592 million people by the year 2035. Foot ulceration continues to be a major comorbidity of diabetes and afflicts as many as 25% of subjects with type 1 and type 2 diabetes during their lifetime. In fact, 2% of the diabetic population annually develop a new ulcer and roughly 85% of all lower extremity amputations in patients with diabetes mellitus are preceded by a foot ulcer. Untreated diabetic foot ulceration and subsequent amputation has a profound impact on the quality of life of the diabetic patient. Those who develop foot ulcer and/or undergo amputation show increased mortality following amputation ranging from 13% to 40% at 1 year, 35% to 65% at 3 years, and 39% to 80% at 5 years. In 2007, the treatment of diabetes and its complications in the US generated at least $116 billion in direct costs; at least 33% of these costs were linked to the treatment of foot ulcers.

Current prevention and treatment options for diabetic foot ulcers (DFU) include pressure reduction on the wound with orthopedic foot-ware, wound care to prevent infections, and wound debridement to remove necrotic debris and re-stimulate the wound healing process. However, studies have reported that the healing rate of DFU over a 12- to 20-week period in response to standard treatment to be between 30% and 60%. Having a quantitative way to assess long-term healing potential from a single initial visit may help triage wounds earlier to more aggressive therapies such as negative pressure therapy, growth factor therapy, hyperbaric oxygen therapy, or surgical intervention. In fact, it has been suggested that the rate of amputation can be reduced by between 49% and 85% with preventative monitoring of the diabetic foot prior to and during ulceration. The cumulative cost of diabetic foot amputation is approximately $70,000 per amputation. Thus, technologies that enable early identification of vascular and tissue compromise leading to ulceration and accurate identification of non-responders to vascular interventions can significantly improve the treatment outcomes and greatly reduce financial burden and personal costs.

Diabetic neuropathy (DN), peripheral vascular disease, and minor foot trauma or infection are typically considered the root cause of DFU. DN inhibits protective sensation and the sweat response, impairs gait control and contributes to foot deformities. This results in excessive shear and pressure due to unnatural gait and foot deformities. PVD can impair blood delivery and effect microvasculature oxygen consumption to the limbs. The combination of inhibited protective/healing response due to denervation and/or poor vascularization permits minor foot trauma or infection to develop into a chronic wound. Evaluation of DN and PVD is essential in identifying patients at risk of ulcer development.

The "Practical guidelines on the management and prevention of the diabetic foot" suggest "areas at risk" of ulceration but to not provide quantitative metrics to identify the risk of ulceration in a specific area. Furthermore, evaluation of DN and PVD cannot be used to assess the severity or healing potential of an already formed ulcer. Therefore, current methods used to assess PVD and DN are not helpful in directing care to an unseen forming wound or a compromised wound healing.

The absence of a reliable tool which can be used by medical professionals to rapidly and reliably determine the health status of tissue is a significant hurdle that impacts both medical research and patient treatment. FIGS. 1A and 1B show examples of tissue that on visual inspection appears healthy, but is clearly compromised according to modulated imaging (MI)-derived wide-field maps. The image on the right shows the resulting tissue failure.

Effective prevention and management of chronic wounds relies on early identification and intervention before the wound worsens and becomes a chronic condition. Perfusion or tissue oxygenation saturation (StO2) is the best and earliest indicator of tissue health and healing, but current measurement methods have serious limitations. Clinicians today rely on direct or indirect measurement methods.

The most common method of measuring perfusion is through clinical impression using the capillary refill test. It gives as quick impression of blood flow to tissue. However, it is just a superficial view, is inaccurate and cannot quantify blood flow to tissue. Because it is superficial, this method cannot see problems at deeper levels (1-5 mm) where problems first form.

Spot sensors provide good measurements over a small (1-2 cm) area, are very expensive ($200+ per disposable probe) and accuracy can vary. As a result, a spot probe can easily miss an area of damaged or unhealthy tissue. A third method, the ankle brachial index (ABI) indirectly measures blood flow and is used as an indicator for perfusion. However, the test is time consuming and according to many clinicians is only useful when the results are at the extremes of the index scale. The ABI also cannot show developing flow problems and for many diabetic patients who have calcified blood vessels the test is useless.

There is simply no existing reliable means of screening a wide area of tissue; particularly skin tissue that may become diseased due to compromised circulation.

Therefore, it is desirable to provide systems and methods direct to a platform technology that provides reliable, robust, intuitive (quantitative) monitoring of tissue oxygenation, giving medical professionals tools to intervene before a region of compromised tissue becomes unsalvageable.

SUMMARY

The various embodiments provided herein are generally directed to the assessment of tissue vascular health. An optical measurement device includes a light source with one or more wavelengths, the light source is configured to illuminate an area of tissue; a detector configured to capture the light reflecting from the tissue at the one or more illumination wavelengths; a processor configured to compute, based on the detected signal, one or more estimates of tissue vascular health, and a display or communication device (e.g., electronic data transfer) configured to store or report the tissue vascular health.

Other systems, methods, features and advantages of the example embodiments will be or will become apparent to one with skill in the art upon examination of the following figures and detailed description.

BRIEF DESCRIPTION OF FIGURES

The details of the example embodiments, including structure and operation, may be gleaned in part by study of the accompanying figures, in which like reference numerals refer to like parts. The components in the figures are not necessarily to scale, emphasis instead being placed upon illustrating the principles of the invention. Moreover, all illustrations are intended to convey concepts, where relative sizes, shapes and other detailed attributes may be illustrated schematically rather than literally or precisely.

FIGS. 25A, 25B, 25C, 25D, 25E and 25F illustrate imaging effects of deep vascular changes and modifications from laser therapy according to embodiments of the present disclosure.

It should be noted that elements of similar structures or functions are generally represented by like reference numerals for illustrative purpose throughout the figures. It should also be noted that the figures are only intended to facilitate the description of the exemplary embodiments.

DETAILED DESCRIPTION

Figures 1A, 1B:
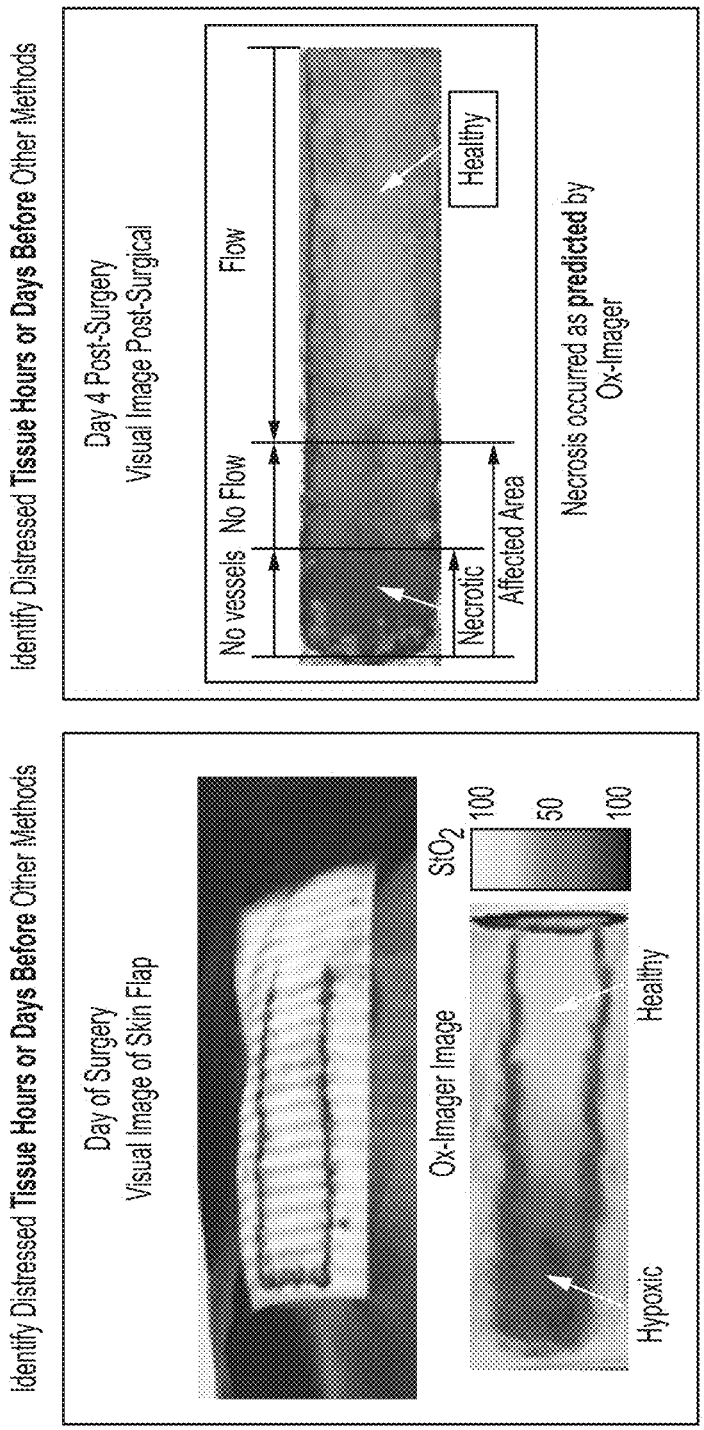
FIGS. 1A and 1B illustrate modulated imaging (MI) images of compromised tissue after surgery and before necrosis is visible to the naked eye.

Each of the additional features and teachings disclosed below can be utilized separately or in conjunction with other features and teachings to provide systems and methods directed to the assessment of tissue vascular health utilizing structured light illumination methods to determine subsurface tissue properties. Such structured light illumination methods may include, but are not limited to, e.g., Modulated Imaging (MI), Spatial Frequency Domain Imaging (SFDI), and the like.

Embodiments of the present disclosure integrate hardware and software solutions to minimize motion artifacts, reduce imaging times, reduce cost, improve light throughput, coregister data, and increase field of view (FOV). Embodiments of the present disclosure acquire snapshot MI data of dorsal and plantar sides of a foot in under 1 second for each side, resulting in a 20× improvement in imaging times coupled with a 50% increase in FOV.

Embodiments of the present disclosure enable mining of historical and new data to develop staging and prediction algorithms based on global and local changes in MI biometrics, including hemoglobin concentration and saturation, water content indicative of edema, and tissue scattering coefficient indicative of structure changes that may compromise healing or cause ulceration.

Representative examples of the embodiments described herein, which examples utilize many of these additional features and teachings both separately and in combination, will now be described in further detail with reference to the attached drawings. This detailed description is merely intended to teach a person of skill in the art further details for practicing preferred aspects of the present teachings and is not intended to limit the scope of the invention. Therefore, combinations of features and steps disclosed in the following detail description may not be necessary to practice the invention in the broadest sense, and are instead taught merely to particularly describe representative examples of the present teachings.

Moreover, the various features of the representative examples and the dependent claims may be combined in ways that are not specifically and explicitly enumerated in order to provide additional useful embodiments of the present teachings. In addition, it is expressly noted that all features disclosed in the description and/or the claims are intended to be disclosed separately and independently from each other for the purpose of original disclosure, as well as for the purpose of restricting the claimed subject matter independent of the compositions of the features in the embodiments and/or the claims. It is also expressly noted that all value ranges or indications of groups of entities disclose every possible intermediate value or intermediate entity for the purpose of original disclosure, as well as for the purpose of restricting the claimed subject matter.

In certain embodiments of the present disclosure, an optical measurement device includes a light source with one or more wavelengths, configured to illuminate an area of tissue, a detector configured to capture the light reflecting from the tissue at the one or more illumination wavelengths, a processor configured to compute, based on the detected signal, one or more estimates of tissue vascular health, and a display or communication device (e.g., electronic data transfer) configured to store or report the tissue vascular health. The estimate of tissue vascular health may include one or more estimates of tissue health and/or risk of tissue injury, based on the concentration, lateral distribution, and/or depth distribution of one or more subsurface tissue constituents exhibiting optical absorption and/or scattering contrast (e.g., blood concentration, blood oxygenation, water/hydration, collagen, lipids, exogenous agents), and/or based on an estimate of vasomotor regulation derived from the one or more tissue constituents exhibiting absorption and/or scattering contrast.

In operation, tissue vascular health may be assessed with a single time point capture. To accomplish such assessment, an area of tissue is illuminated by a light source with one or more wavelengths, light reflecting from the tissue at the one or more illumination wavelengths, estimates of tissue vascular health are computed from the detected or captured light signals, and the computed estimate of tissue vascular health is displayed for review.

The source of the optical measurement device may be configured to create at least one spatially-structured light pattern over the tissue surface. The detector may be a 2D imaging detector array (such as, e.g., a CCD/CMOS camera). The detector may be a single-element detector (such as, e.g., a photodiode or an optical fiber relay to a detection system), such as the detection system described and claimed in U.S. Pat. No. 9,220,412, which is incorporated herein by reference as if set forth in full. Alternatively, multiple single-element detectors may be configured to collect reflected light from multiple tissue locations. The display may be an interactive touchscreen device, tablet, or digital phone. The optical measurement device may be configured to interface with a computer system, tablet, or digital phone with a wired or wireless connection.

In operation, a diagnosis of tissue health and/or risk is generated, and a recommendation of a therapy, treatment, product, or behavioral change is provided.

Modulated imaging (MI), is a novel non-contact optical imaging technology that was invented at the Beckman Laster Institute. MI has the unique capability of spatially resolving optical absorption and scattering parameters, allowing wide-field quantitative mapping of tissue optical properties. By separating and quantifying the multi-spectral absorption and scattering optical properties, MI removes the cross talk in reflectivity changes resulting from physically distinct contrast mechanisms, and provides a more direct assessment of tissue state and predictive power via derivation of physiologically relevant parameters.

While compatible with temporally-modulated photon migration methods, MI alternatively uses spatially-modulated illumination for imaging of tissue constituents. Periodic illumination patterns of various spatial frequencies are projected over a large (many cm$^2$) area of a sample. The reflected image differs from the illumination pattern due to the optical property characteristics of the sample. Typically, sine-wave illumination patterns are used. The demodulation of these spatially-modulated waves characterizes the sample modulation transfer function (MTF), which embodies the optical property information. Accelerated Monte Carlo-based analysis of MTF data results in 2D maps of the quantitative absorption ($\mu_a$) and reduced scattering ($\mu_s'$) optical properties. Mapping the absorption coefficient at multiple wavelengths enables quantitative spectroscopy of tissue chromophores such as oxy- and deoxy-hemoglobin and water (ctO$_2$Hb, ctHHb, and ctH$_2$O) and derived physiology parameters such as tissue oxygen saturation and blood volume (stO$_2$ and ctTHb). The spatially-varying phase can also be measured, yielding topological surface information. This enables visualization of the 3D tissue profile, as well as calibration data for accommodating curved surfaces in the analysis.

Figures 2A, 2B, 2C:
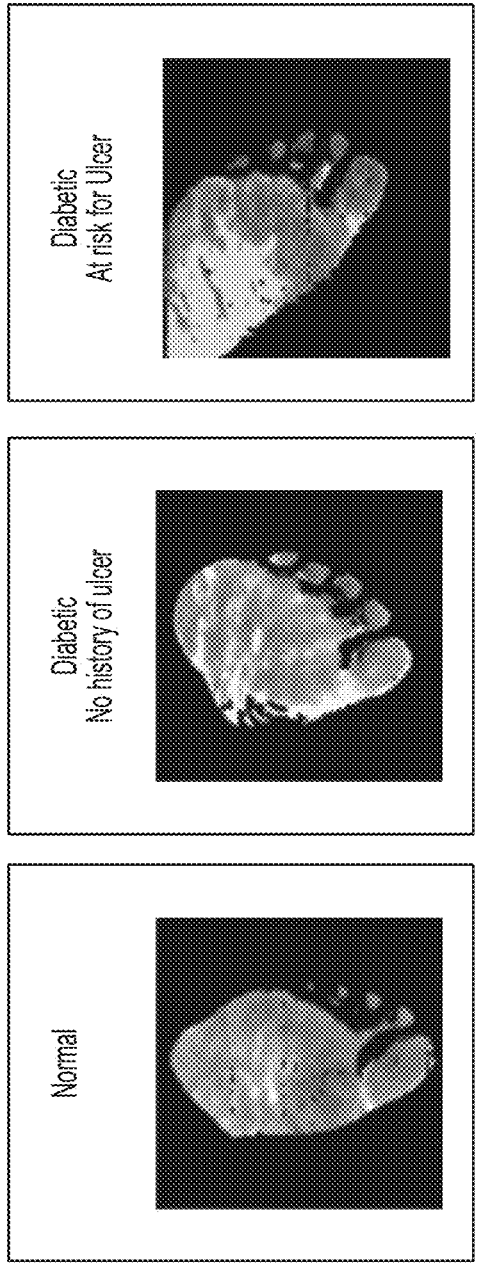
FIGS. 2A, 2B and 2C illustrate modulated imaging (MI) images of a non-diabetic healthy foot, a diabetic with a healthy foot, and a diabetic with a high risk of ulcer formation.

FIGS. 2A and 2B illustrate modulated imaging (MI) images of a non-diabetic healthy foot (left) a diabetic with a healthy foot (center) and a diabetic with a high risk of ulcer formation (right).

Figure 3:
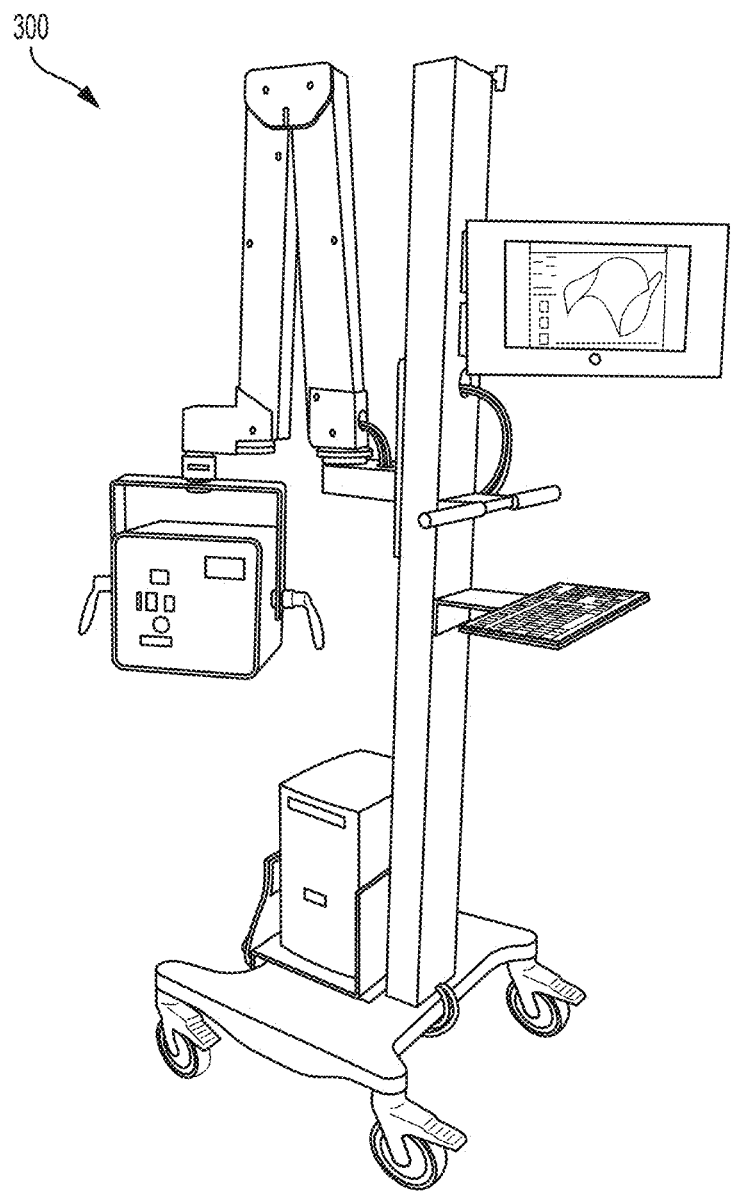
FIG. 3 illustrates an example embodiment of an optical measurement device for use with embodiments of the present disclosure.

FIG. 3 illustrates an example embodiment of an optical measurement device for use with embodiments of the present disclosure. The exemplary optical measurement device 300 is a general-purpose modulated imaging research user only (ROU) system designed for both pre-clinical and clinical research. The device 300 is capable of measuring absorption and scattering maps using eleven LED wavelengths spanning the visible to NIR range (400-980 nm) over large fields of view (15×20 cm). These wavelengths are selected for their sensitivity for quantitation of melanin, deoxygenated hemoglobin, oxy-hemoglobin, and water.

Microcontroller electronics synchronize with LED pulses with DMD projection and camera acquisition, enabling rapid image sequence capture of all spatial patterns and wavelengths. The device 300 is capable of acquiring data with ~15 ms integration time per image. A typical sequence of images (11 wavelengths, 5 spatial frequencies~165 images) take a total of ~20 seconds to acquire data and is reducible to is for DFU. The device 300 includes simultaneous collection of surface topology measurements and tissue color (RGB) photographs for calibrated, color-balanced illumination, enabling a standardized method of comparing MI results with visual clinical impression. The device 300 can also be used in IACUC and IRB-approved studies studying applications including burn wounds, skin flaps, decubitus ulcers, cancer, and dermatology.

Figure 4A:
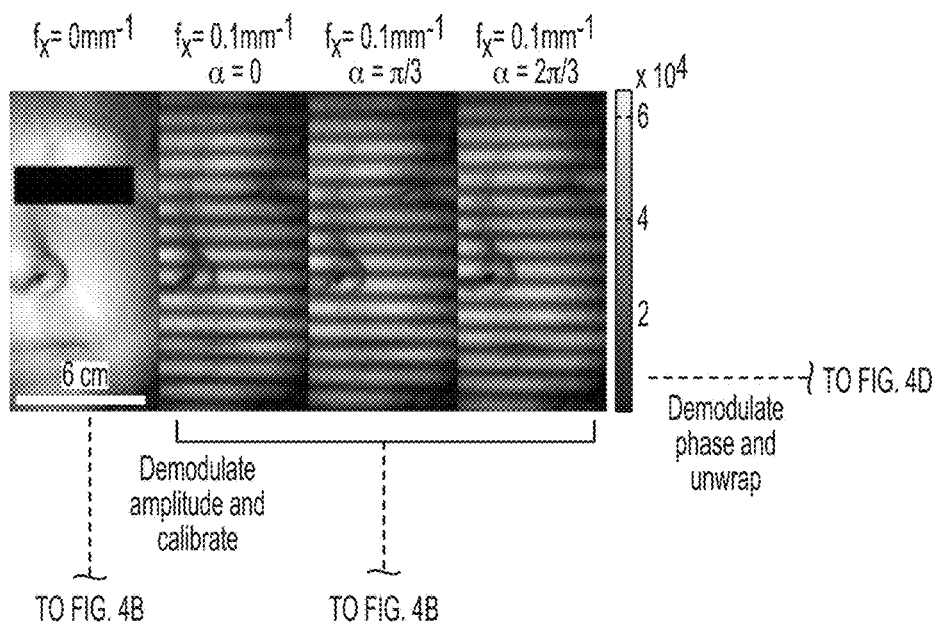
FIGS. 4A, 4B, 4C and 4D illustrate a flowchart of modulated imaging (MI) data for use with embodiments of the present disclosure.
Figure 4B:
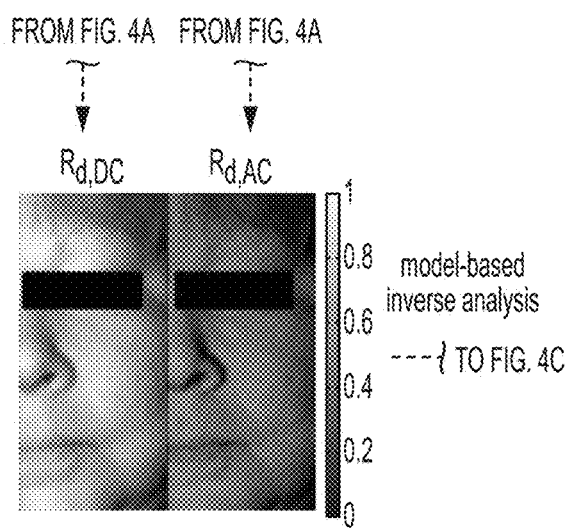
Figure 4D:
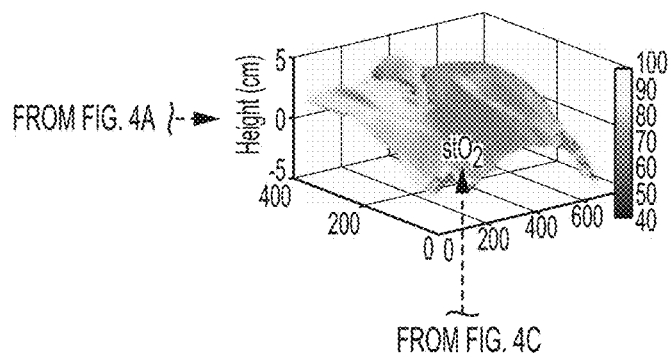
Figure 4C:
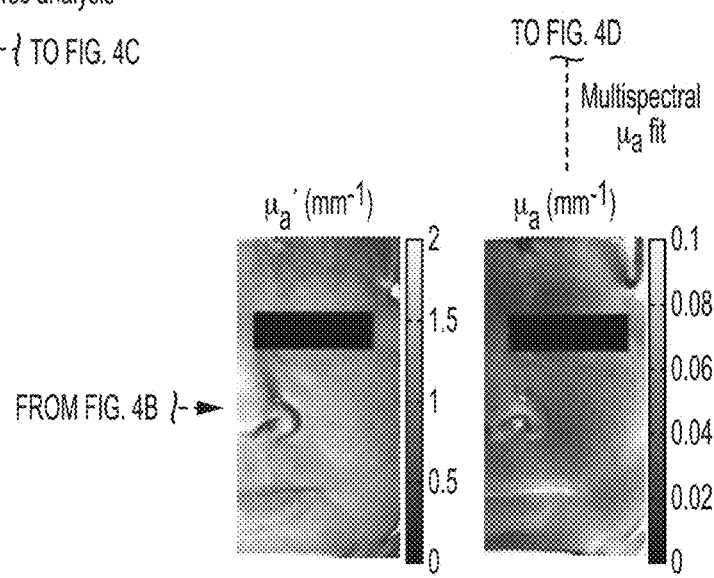

FIGS. 4A, 4B, 4C and 4D illustrate a flowchart of modulated imaging (MI) data processing for use with embodiments of the present disclosure. In FIG. 4A, modulated intensity patterns are projected onto the surface at each frequency (three phase images per frequency). In FIG. 4B, the patterns are amplitude demodulated and calibrated. In FIG. 4C, the patterns are fit to a multi-frequency model to determine optical properties. In FIG. 4D, separately phase demodulation provides information on tissue height, which can be used for both curvature calibration and visualization. Data are processed separately for each pixel, generating spatial maps of optical properties.

Figures 5A, 5B:
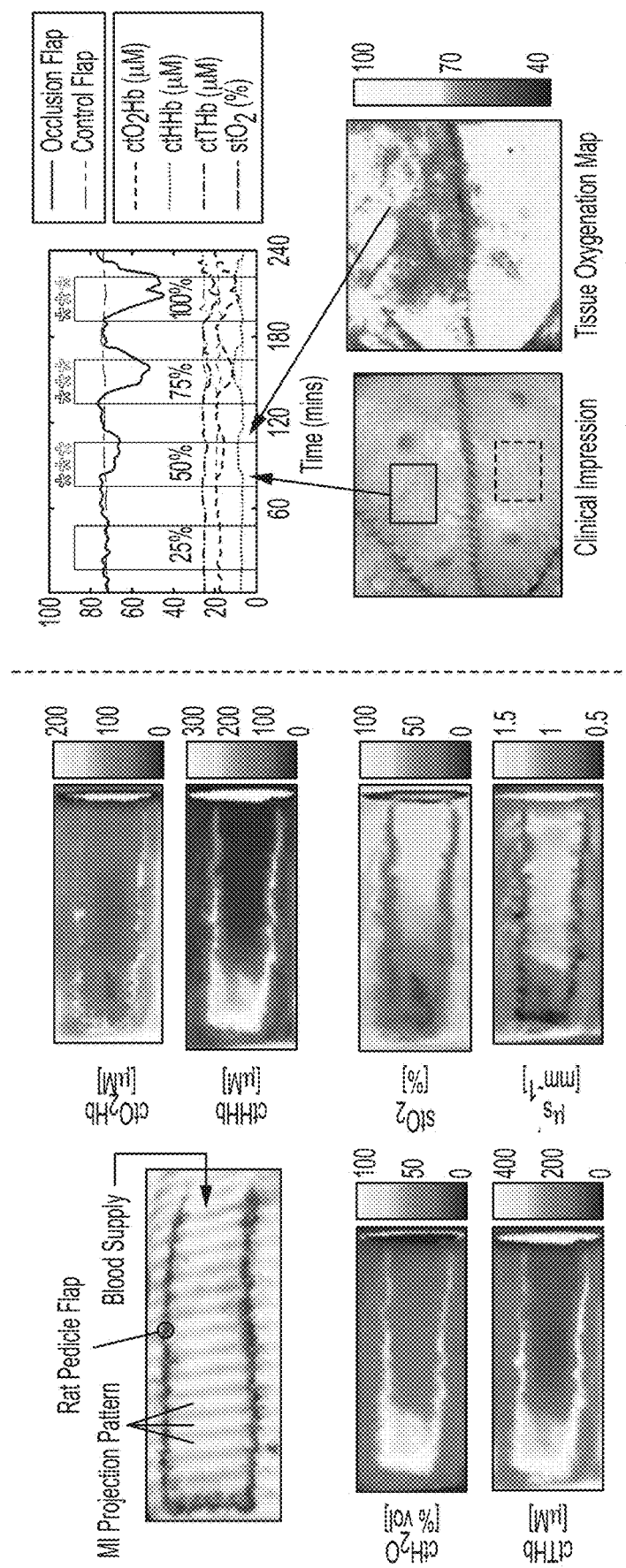
FIGS. 5A and 5B illustrate measurements of gradient changes in perfusion, according to embodiments of the present disclosure.

FIGS. 5A and 5B illustrate measurements of gradient changes in perfusion, according to embodiments of the present disclosure. In FIGS. 5A and 5B, a rodent McFarlane dorsal pedicle flap model was used to demonstrate the ability to measure gradient changes in perfusion. In FIG. 5A, MI measured decreased oxygenation and increased blood pooling at the distal end of the flap where flow was most compromised. Additionally, an increase in water content (i.e., edema) and decrease in reduced scattering (i.e., early necrosis) are observed at the distal end of the flap. MI measures of scattering and tissue water content provide novel measures of tissue health and improve accuracy of tissue hemoglobin and oxygen saturation by removing cross-talk. In FIG. 5B, early detection of compromised perfusion in flaps using a porcine model are demonstrated. Flap perfusion was isolated to a single group of arteries and vein for each flap and inflow/outflow were systematically controlled with an implanted occlusion balloon and a flow sensor. MI parameters demonstrated sensitivity to small changes in vascular inflow during a series of controlled levels of arterial occlusion. MI detected changes in flow prior to clinical impression, as recorded by calibrated color photography. MI also revealed perfusion for partial occlusions varied spatially. MI $stO_2$ showed strong correlation with simultaneous measurements with an FDA-cleared NIRS tissue oximeter. MI was able to differentiate between arterial and venous congestion based on oxy- and deoxy time traces.

Figures 6A, 6B:
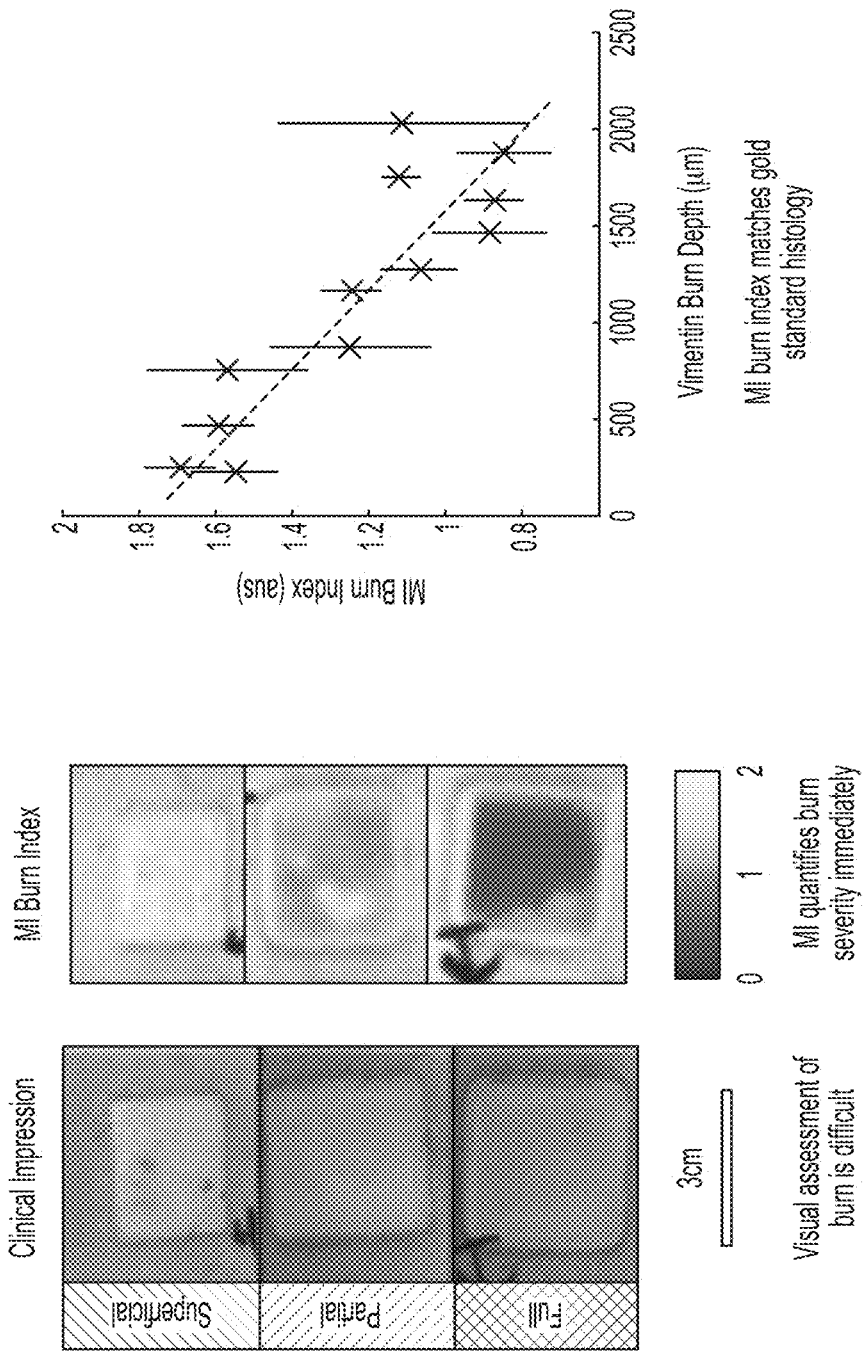
FIGS. 6A and 6B illustrate derived SFDI outputs used to develop a burn index map, according to embodiments of the present disclosure.

FIGS. 6A and 6B illustrate derived SFDI outputs used to develop a burn index map, according to embodiments of the present disclosure. In FIGS. 6A and 6B, multiple burn wounds of three severities (superficial partial thickness, deep partial thickness and full thickness) are shown in a porcine model over the course of 72 hours. Differential contrast was observed for the many parameters that MI measures ($ctO_2Hb$, $ctHHb$, $stO_2$, scattering). Functional parameters such as $stO_2$ and $ctHHB$ evolved over the course of 72 hours and were statistically differentiable from each other ($p<0.01$) at this time. The reduced scattering contrast was a much more stable measurement. A reduction in scattering was measured that correlated with burn depth as measured by histology ($r2=0.94$). This scattering is believed to be sensitive to the phase change of the collagen fibrils as they are thermally denatured and broken down. Derived SFDI outputs (absorption and scattering) were combined to create a burn index map that correlates with burn depth. A burn index can predict burn wound outcome and provide early treatment guidance to clinicians (i.e., self-healing vs. graft).

Figure 7B:
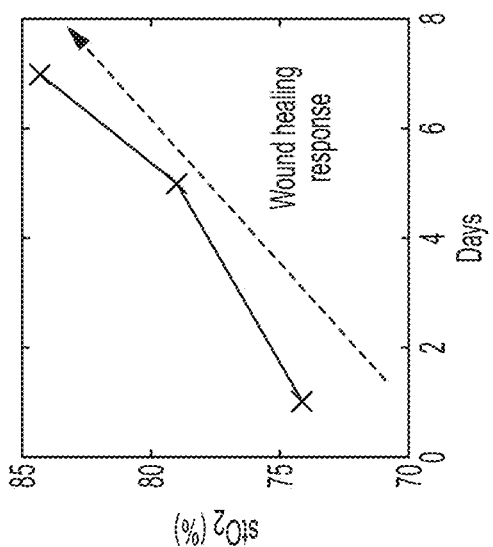
FIGS. 7A and 7B illustrate time course measurements of a burn, according to embodiments of the present disclosure.
Figure 7A:
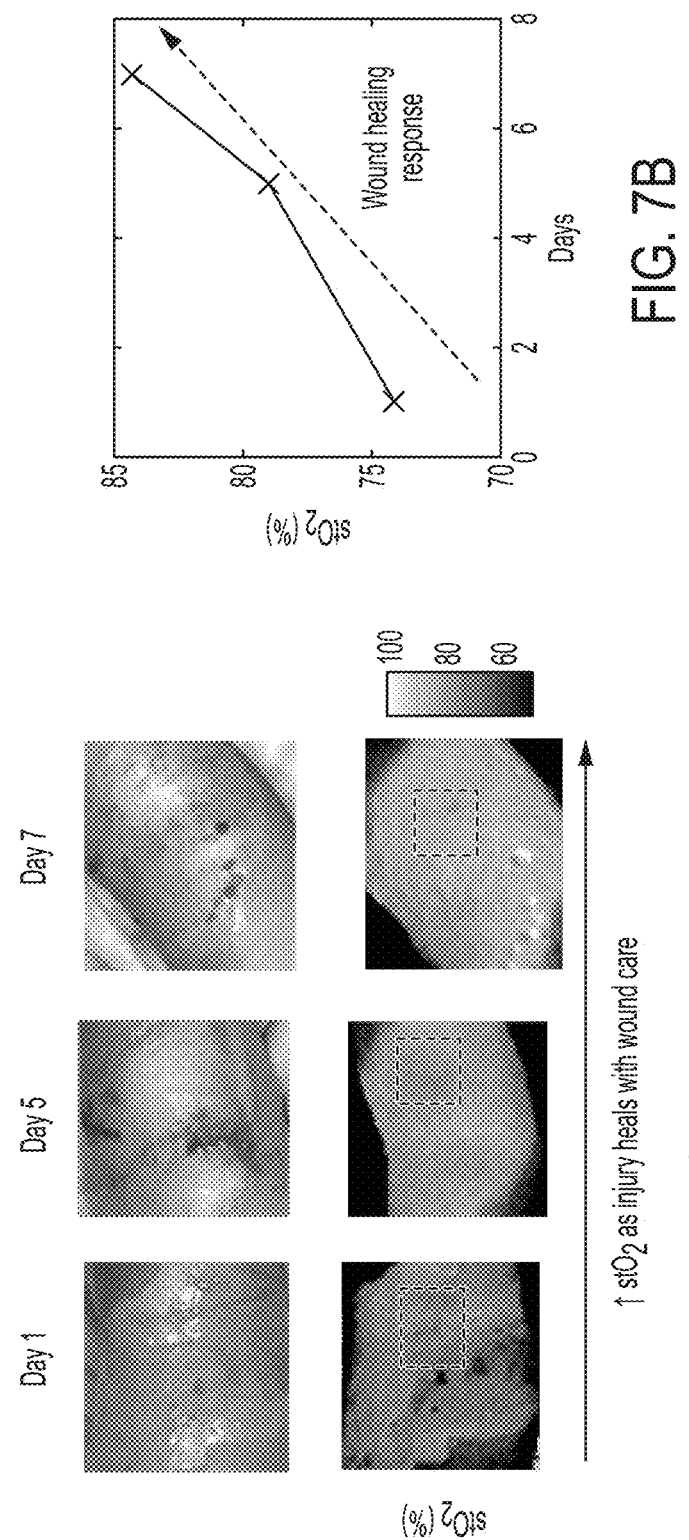

FIGS. 7A and 7B illustrate time course measurements of a burn, according to embodiments of the present disclosure. In the superficial thickness wound of FIG. 7A, a steady increase in oxygen saturation over time is observed in the burn wound. This is a strong indicator of the tissue healing process in burn injuries and is linked to eventual outcome.

Figures 8A, 8B, 8C:
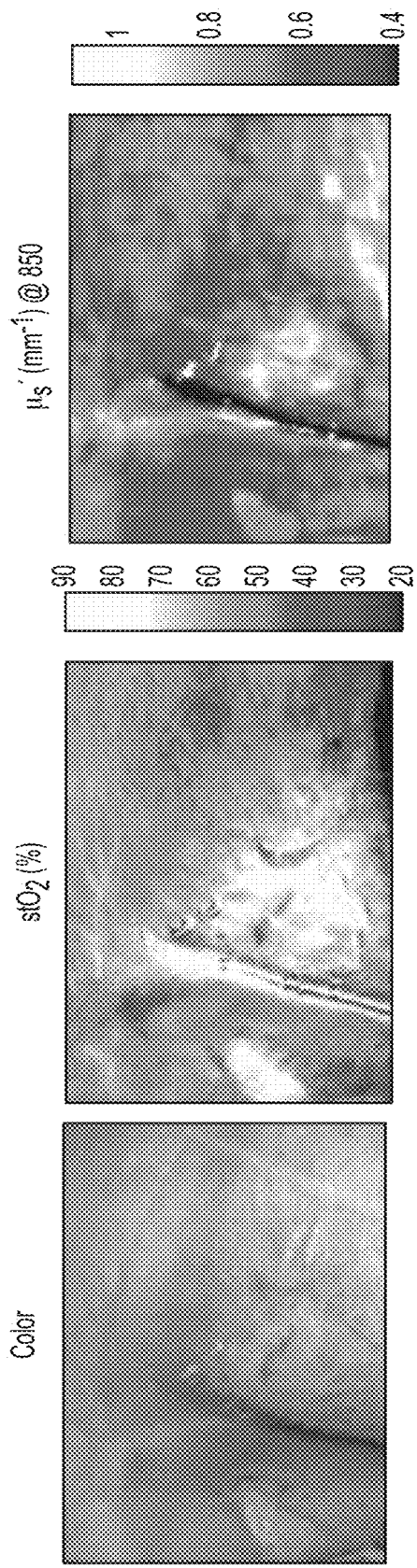
FIGS. 8A, 8B and 8C illustrate a photograph of an unstageable decutibus ulcer and MI derived maps of tissue oxygenation and scattering, according to embodiments of the present disclosure.

FIGS. 8A, 8B and 8C illustrate photographs of an unstageable decutibus ulcer and MI derived maps of tissue oxygenation and scattering, according to embodiments of the present disclosure. A clinically unstageable decubitis ulcer in a 69-year-old patient is shown in FIGS. 8A, 8B and 8C. A color photograph (FIG. 8A) is shown and compared to a MI-derived map of deep-tissue $stO_2$ (FIG. 8B). The color photo indicates an ambiguous, pink state with ruptured epidermis. The oxygenation map indicates a more specific diffuse zone of hyper-saturation extending beyond the visible dermal damage to the periwound area, potentially indicating the extent of inflammation in a wound-healing response. A co-located but distinctly smaller zone of increased scattering (FIG. 8C) may indicate matrix structural modifications at the center of the wound area from tissue repair (granulation tissue has been found to have a high scattering coefficient).

Figure 9:
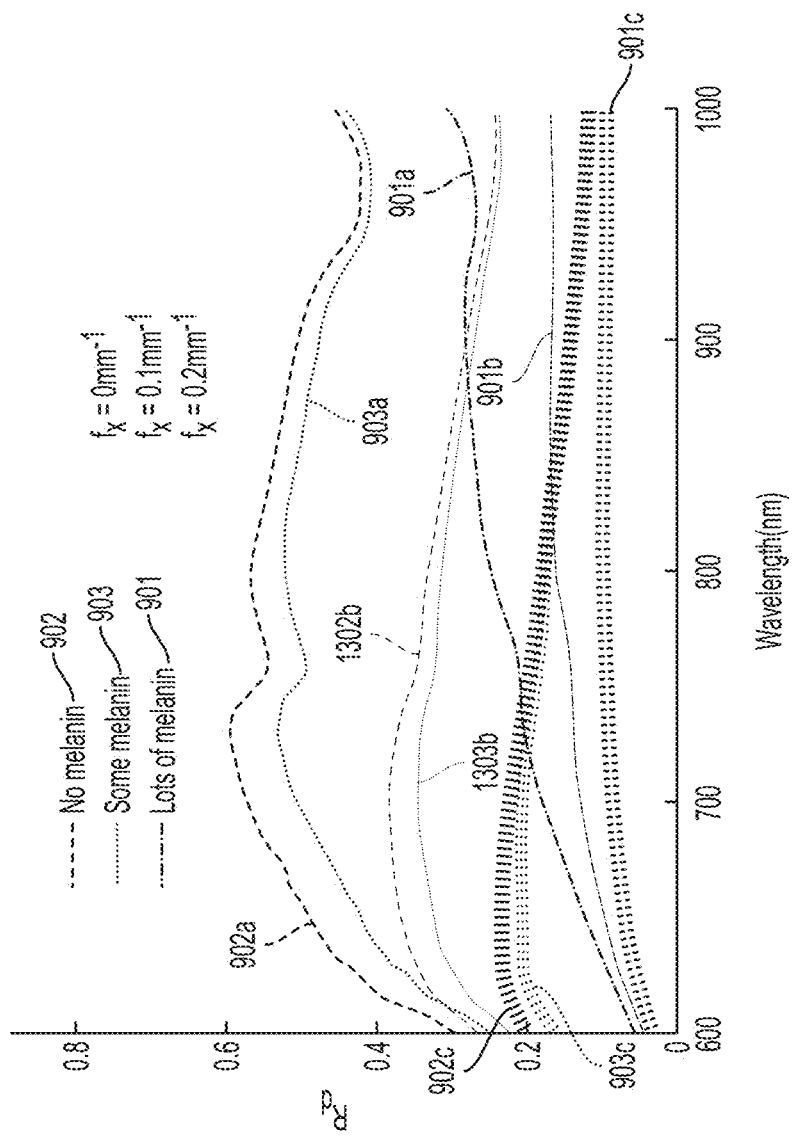
FIG. 9 illustrates examples of SFD spectra for varying melanin concentrations and spatial frequencies.

FIG. 9 illustrates examples of SFD spectra for varying melanin concentrations and spatial frequencies. Development of advanced multi-layer multi-spectral models using MI resulted in the ability to generate forward simulated MI spectra for multiple skin types and perform simulations to determine sensitivities of the recovered MI signals to chromophore changes in each layer.

MI data has led to development of a brand-new spatial frequency domain (SFD) Monte Carlo simulation code capable of directly simulating Modulated Imaging SFD data for multi-layered tissues. This code allows "native" frequency-domain tallies of exiting photons, and removes significant aliasing problems associated with traditional methods relying on Fourier-transformation of real-domain (e.g., $R(\rho)$ or "source-detector") data. Using a combination of White Monte Carlo (rapid adjustment of tissue absorption), spatial rescaling (rapid adjustment of tissue scattering and spatial frequency), and lookup tables, a novel method of accelerating the simulations has been developed. The end result is an algorithm that takes only~1 ms per curve to calculate tissue reflectance from an arbitrary number of layers, layer thicknesses, and layer optical properties. A "classic" Monte Carlo simulation with the same data fidelity would require 2.5 hours, representing a speedup factor of approximately $10^8$.

In FIG. 9, SFD spectra is shown for a concentration of no melanin (902, lines 902a, 902b, 902c), some melanin (903, lines 903a, 903b, 903c) and lots of melanin (901, lines 901a, 901b, 901c). Based on these results, the internal light penetration and sensitivities of the detected photons to changes of chromophores were determined in each layer including epidermis, dermis, and sub-cutaneous tissues.

Figure 10B:
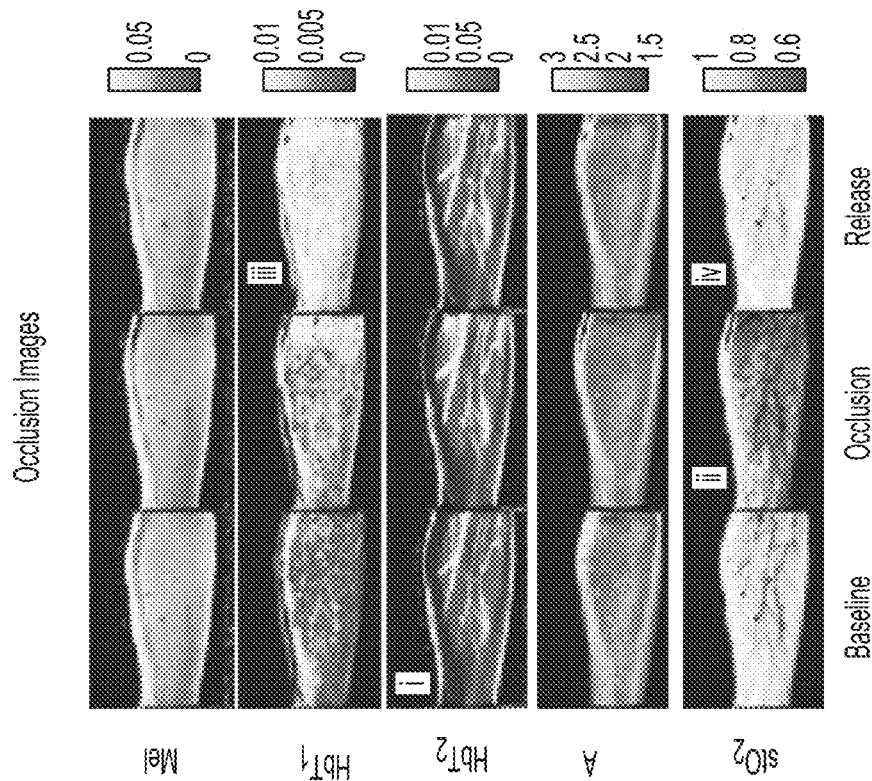
FIGS. 10A and 10B illustrate a three layer geometry developed for skin imaging, for use with embodiments of the present disclosure.
Figure 10A:
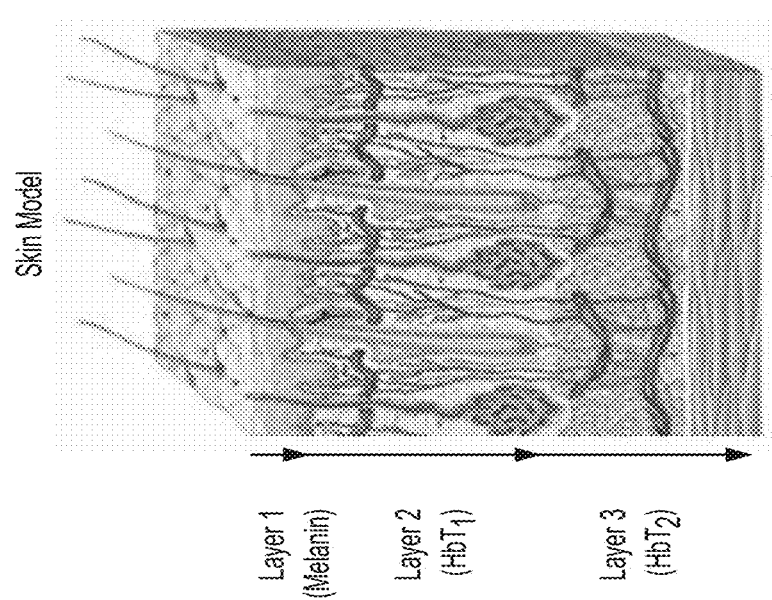

FIGS. 10A and 10B illustrate a three layer geometry developed for skin imaging, according to embodiments of the present disclosure. Previous publications have validated depth-homogeneous sampling for dynamic $stO_2$ measurements; however, melanin remained a confounding factor when analyzing skin data. In addition, superficial hemoglobin changes (e.g., hyperemia in the papillary dermis) would appear washed out with very low contrast. In FIGS. 10A and 10B, which illustrate a 3-layer geometry developed for skin aging using MI, light transport in the visible and near infrared regime were modeled using Monte Carlo models of light transport in the Spatial Frequency Domain. Validated transport computational codes were adopted from the Virtual Photonics Technology Initiative, an open-source software project for biophotonics at UC Irvine. In FIG. 10A, a new three layer skin model is applied to an arteriovenous arm-cuff occlusion measurement. In FIG. 10B, recovered MI parameters highlight differentiation between superficial and (i) deep hemoglobin. During occlusion, $stO_2$ is reduced dramatically and then upon release recovers with an (iii, iv) influx of oxygenated hemoglobin during reactive hyperemia.

Figures 11A, 11B:
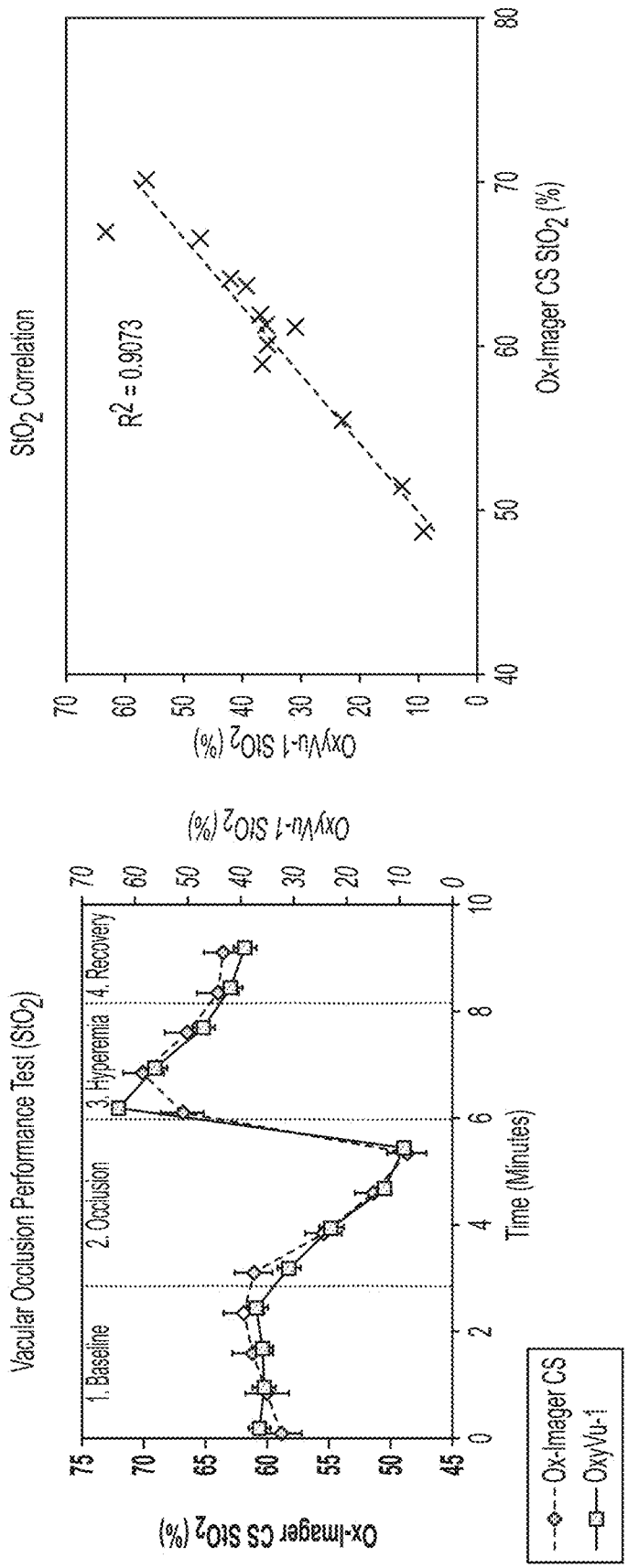
FIGS. 11A and 11B illustrate a correlation of mean values and standard error of StO2 measured by Ox-Imager CS and OxyVu-1.

FIGS. 11A and 11B illustrate a correlation of mean values and standard error of $StO_2$ measured by Ox-Imager CS and OxyVu-1. Subjects of skin types (Fitzpatrick I-VI) were occluded and chromophores were measured at baseline, during occlusion and release for both the Ox-Imager and a FDA predicate device, the HyperMed OxyVu-1. Measured tissue oxygenation shows significantly reduced oxygen saturation during cuff occlusion, and hyperemia upon release. Although, absolute values are different between devices, that characteristic shape of a vascular occlusion test between the systems demonstrate a strong correlation ($r^2>0.9$). The difference in absolute values is due to deeper tissue penetration of the signals using the Ox-Imager system.

Figures 12A, 12B:
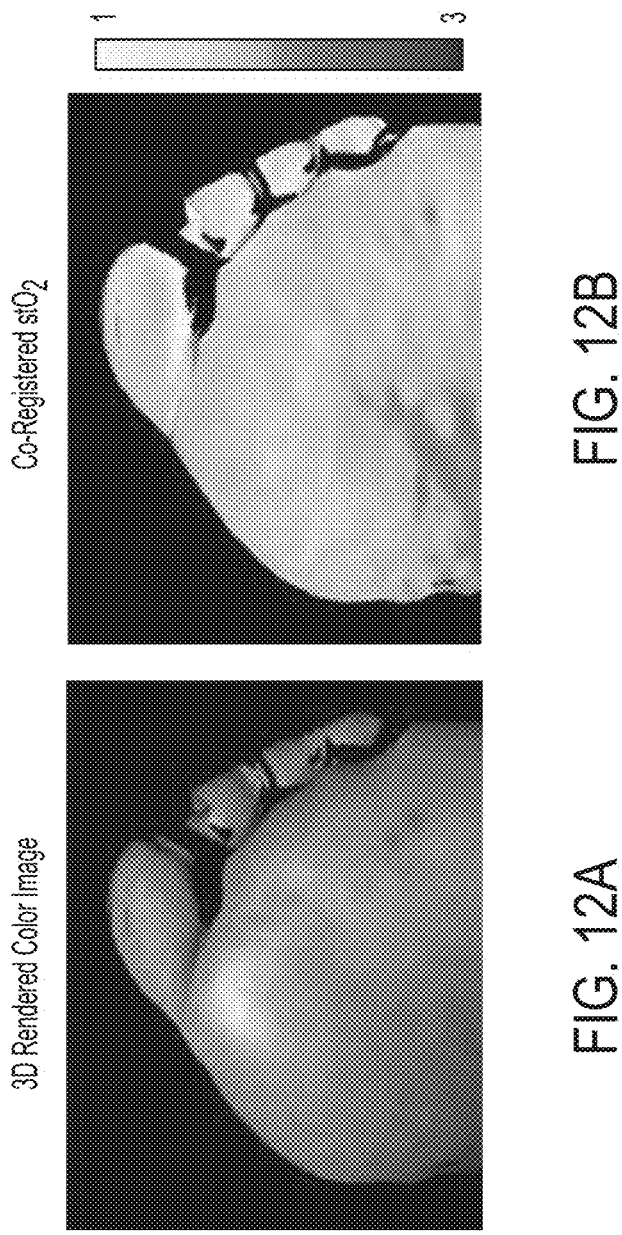
FIGS. 12A and 12B illustrate 3D renderings of a foot with core-registered tissue oxygen saturation map.

FIGS. 12A and 12B illustrate 3D renderings of a foot with core-registered tissue oxygen saturation map. Multi-height correction is a critical component of MI data analysis. The complex geometry of feet can affect the interpretation of results if this is not dealt with in an appropriate manner. Structured illumination is used to reconstruct tissue height and apply corrections to the data to improve accuracy.

Figure 13:
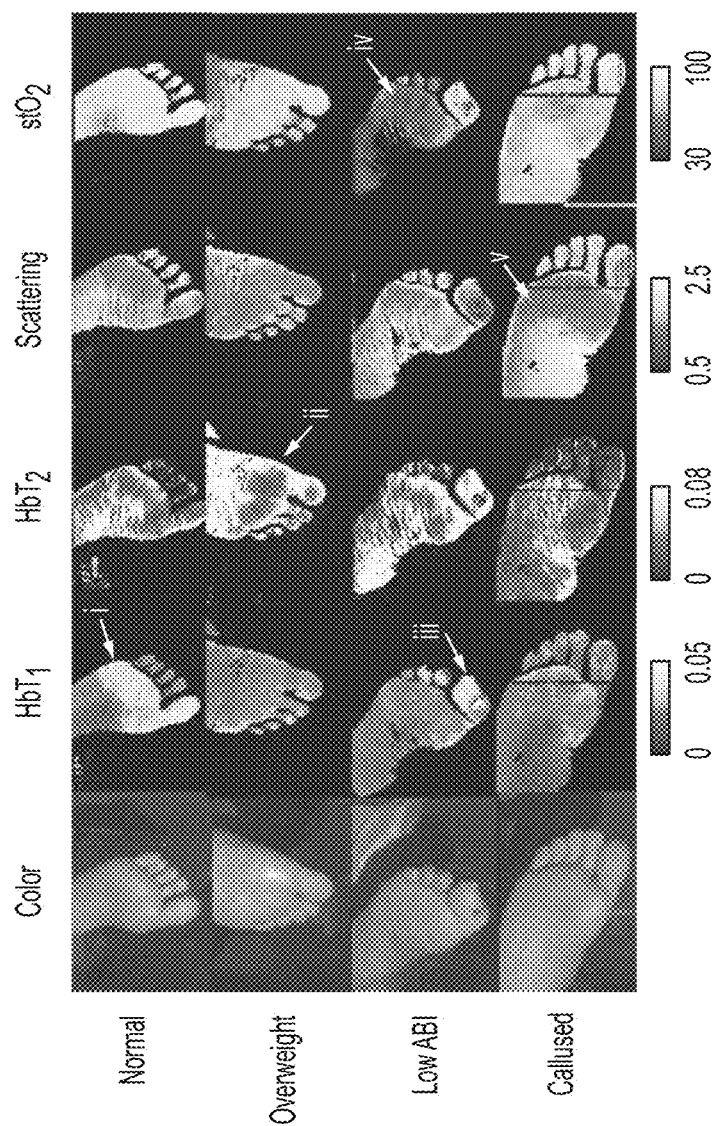
FIG. 13 illustrates a collage of preliminary foot data showing a variety of hemoglobin and oxygen saturation levels.

FIG. 13 illustrates a collage of preliminary foot data showing a variety of hemoglobin and oxygen saturation levels. For a normal foot, elevated superficial hemoglobin is observed in the pads (i) of the feet along with homogeneous saturation across the surface of the foot. In an overweight diabetic patent, decreased levels of deep hemoglobin (ii) are observed at the pressure points in the pads of the feet and high levels in the arch of the foot. For a patient with a low ABI (ABI=0.70), elevated levels of deep hemoglobin are observed throughout the foot with low oxygenation (iv)—except for a small area that has an ulcer—which has elevated superficial hemoglobin (iii) and oxygen saturation in the peri-wound. In the case of a callused foot, a decrease in scattering (v) is observed compared to surrounding area in the callused area—a possible result of epidermal thickening.

Figures 14A, 14B:
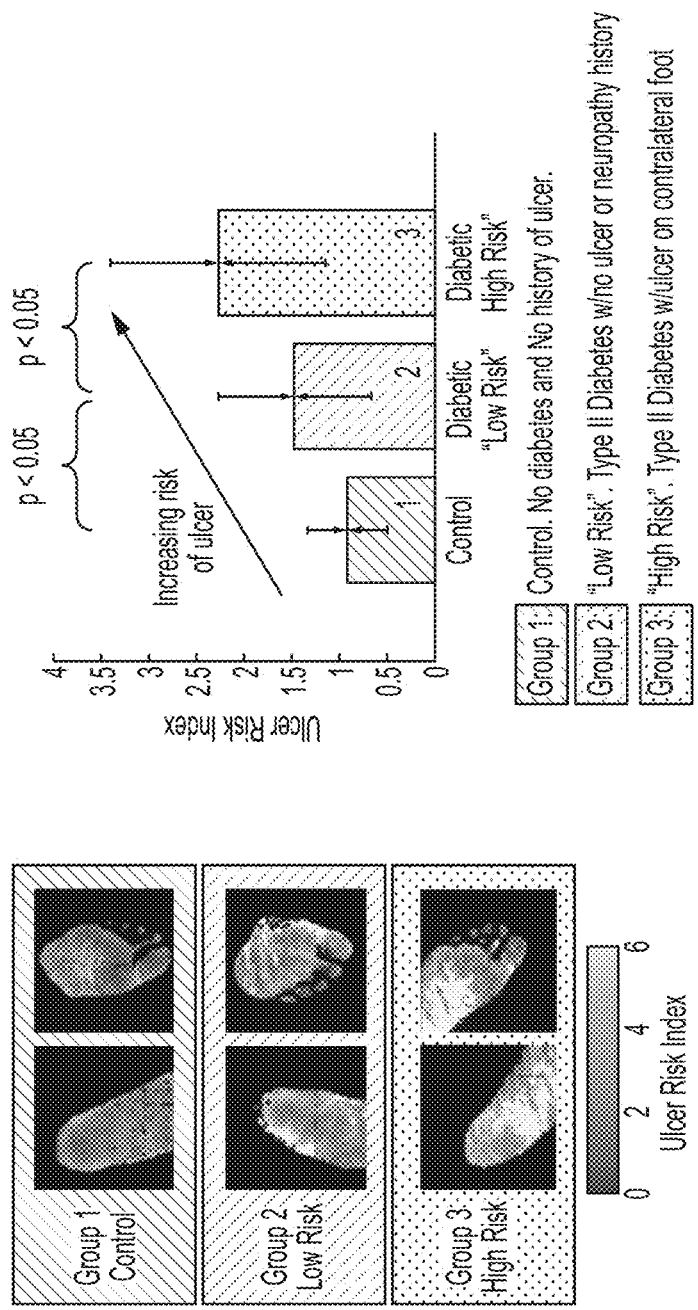
FIGS. 14A and 14B illustrate the use of MI biometrics to create an ulcer risk index that stratifies ulcer risk in subjects.

FIGS. 14A and 14B illustrate the use of MI biometrics to create an ulcer risk index that stratifies ulcer risk in subjects. Imaged feet were divided into 3 cohorts: 1) a control group with no diabetes and no history of ulceration, 2) a "low risk" group with type II diabetes and no neuropathy and history of ulceration, and 3) "high risk" group with type II diabetes and ulcer on the contralateral foot. Using biometrics measured by the present system, an ulcer risk index was built based primarily on the ratio of superficial and deep hemoglobin. Initial analysis, shown in FIGS. 14A and 14B, shows that "high risk" cohort has elevated levels of deep hemoglobin and low levels of superficial hemoglobin—measurement outputs that are unique to the present system. It is believed that the pooling effect can be explained by poor vasomotor regulation of the capillaries likely caused by their health status. Furthermore, analysis shows that each cohort can be distinguished based on the distributed index value in the foot based on average image values.

Figure 15:
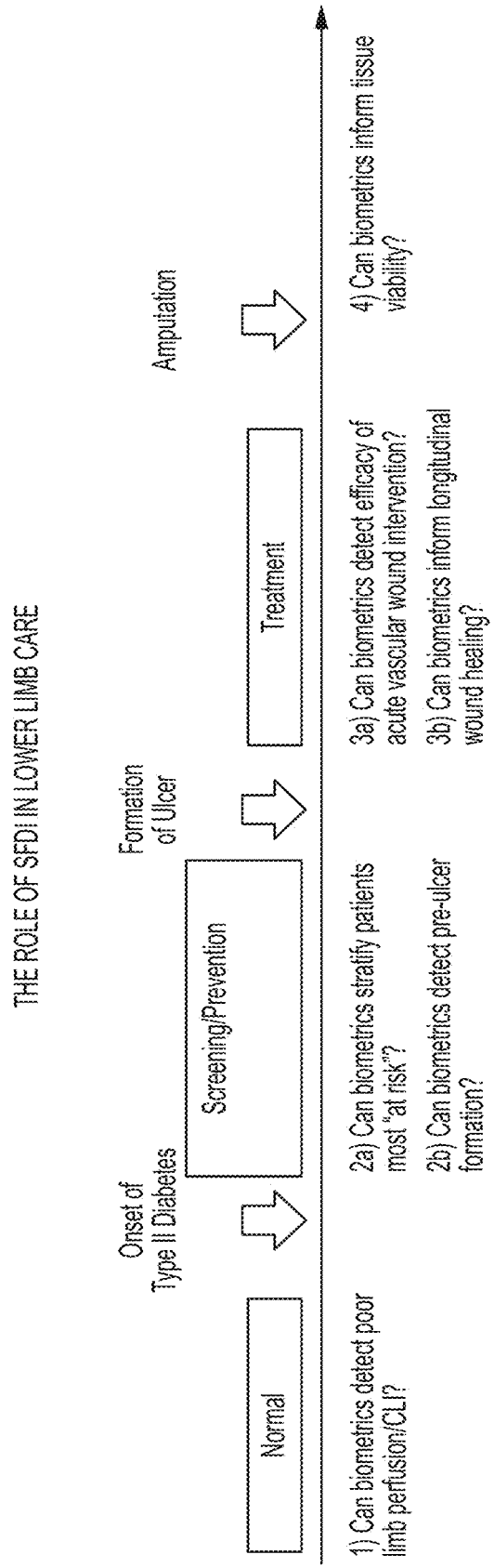
FIG. 15 illustrates a timeline of the role of SFDI in lower limb care, based on embodiments of the present disclosure.

FIG. 15 illustrates a timeline of the role of SFDI in lower limb care, based on embodiments of the present disclosure. Biometrics can be used from normal health situations to onset of type II diabetes, to formation of ulcer, to amputation phases. Biometrics aid in detection and inform therapies.

Figure 16B:
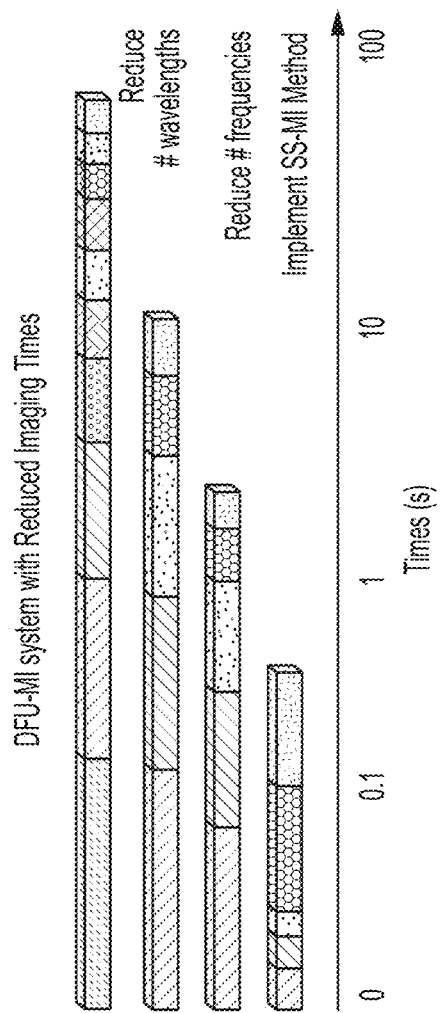
FIGS. 16A and 16B illustrate an expanded field of view and reduced imaging times according to embodiments of the present disclosure.
Figure 16A:
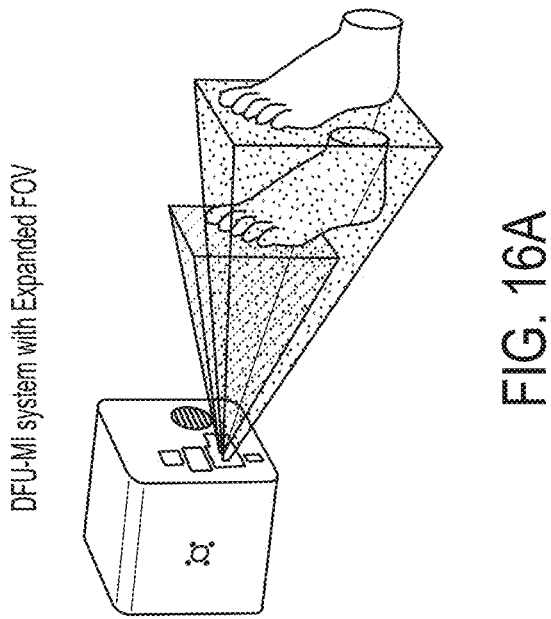

FIGS. 16A and 16A illustrate an expanded field of view and reduced imaging times according to embodiments of the present disclosure. In FIG. 16A, field of view is expanded from 20×15 cm to 50% larger to capture the entire foot in a single snapshot. A larger field of view puts greater demand on optical output and requires improvement in light throughput to keep exposure times short (<10 ms) so the measurements are insensitive to ambient room lights. For foot measurement, a 5-wavelength and single spatial frequency measurement is equivalent to a current 10 wavelength, 5 frequency measurement. Thus, more dies on the LED boards can be dedicated to the core wavelengths and structured and planar light can be combined to improve light throughput by a factor of 10. With this reduction, the total number of images in a sequence is 8 instead of 150. In FIG. 16B, step by step improvements are shown as well as how the changes reduce total imaging times 10-fold (from ~20 ms to <500 ms). These changes enable imaging in ambient room-light conditions, reduce the effects of motion artifacts, and improve long-term component reliability by reducing complexity.

Figure 17:
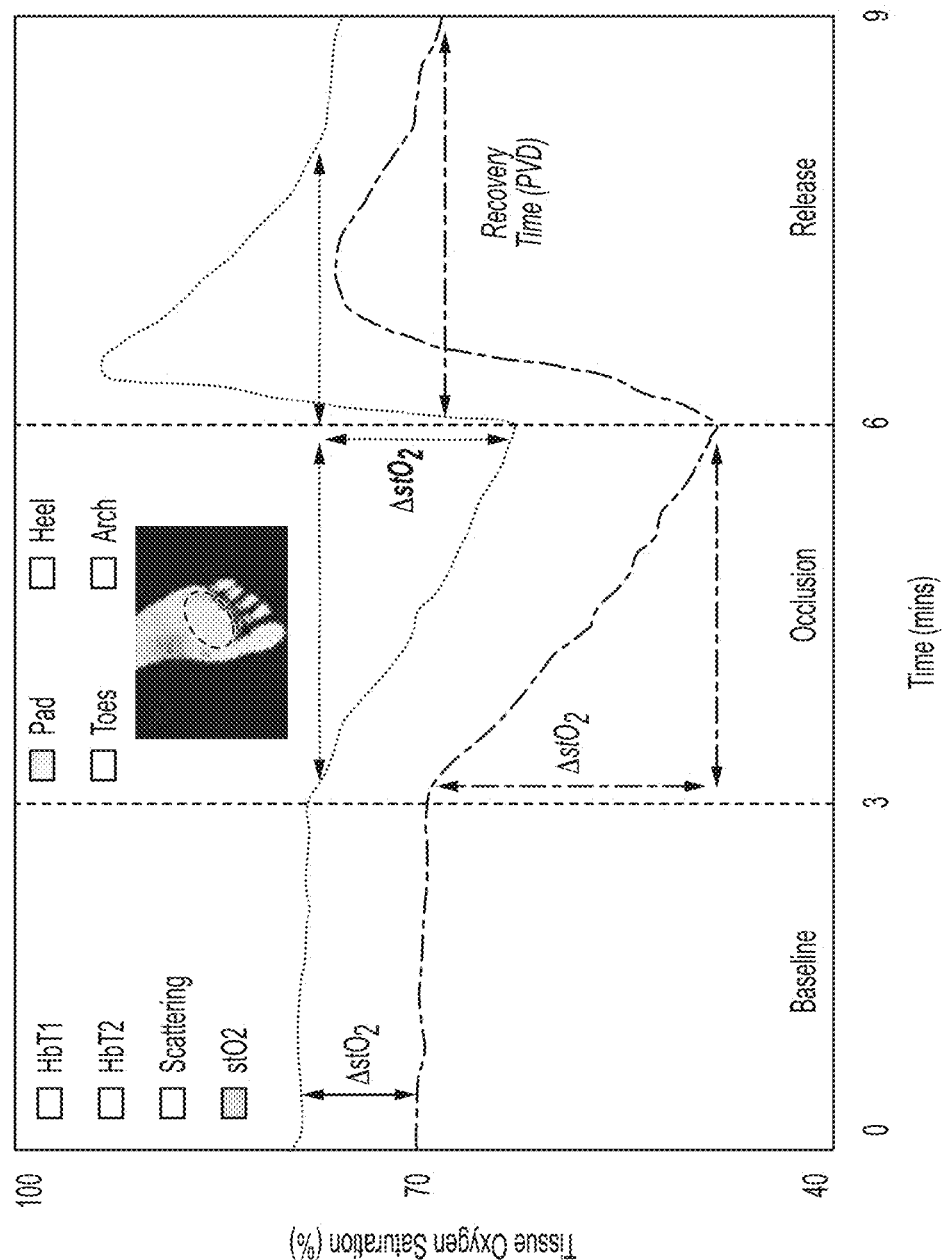
FIG. 17 illustrates a test results from a vascular reactivity study of a foot, according to embodiments of the present disclosure.

FIG. 17 illustrates test results from a vascular reactivity study of a foot, according to embodiments of the present disclosure. Dynamic measurements during ABI cuff challenge allow for the establishment of benchmarks for MI biometrics before, during, and after occlusion on the plantar side of the foot.

Figure 18:
FIG. 18 illustrates an example clinical assessment worksheet for use with embodiments of the present disclosure.

FIG. 18 illustrates an example clinical assessment worksheet for use with embodiments of the present disclosure. According to one assessment, 25 diabetic subjects with a history of an ulcer are following monthly for 12 months as indicated in table 1 below. The worksheet in FIG. 18 is used to record (i) the location of each previous ulceration, (ii) locations and reasons for other potential regions ono the subject's foot that may be at risk for ulceration in the next 6 months, and iii) risk category for the subject. H indicates a healed ulcer, P indicates a persistent ulcer, and D indicates danger of ulceration.

TABLE 1

Imaging session for 25 patient longitudinal study to assess DFU wound healing.

| Visit | 1 | 2 | 3 | 4 | 5 | 6 | 7 | 8 | 9 | 10 | 11 | 12 |
|---|---|---|---|---|---|---|---|---|---|---|---|---|
| Imaging | • | • | • | • | • | • | • | • | • | • | • | • |
| Assessment | • | • | • | • | • | • | • | • | • | • | • | • |

Figure 19A:
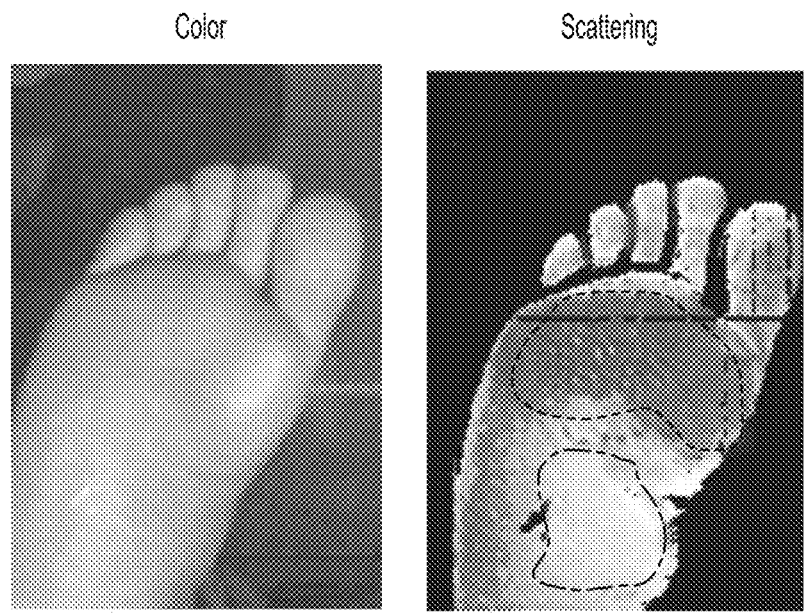
FIGS. 19A and 19B illustrate distribution of scattering in a callused foot, according to embodiments of the present disclosure.
Figure 19B:
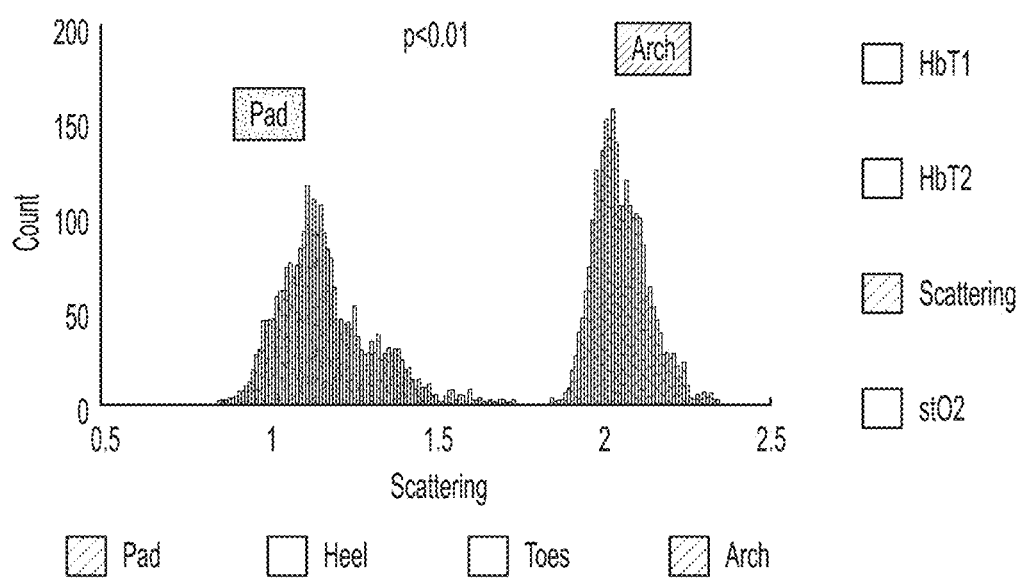

FIGS. 19A and 19B illustrate a distribution of scattering in a callused foot, according to embodiments of the present disclosure. The pads and arch of the plantar feet are identified and a histogram distribution is generated of the scattering values. Distribution of scattering in the callused foot shows lower scattering at pressure points—perhaps an indication that a pre-ulcer callus has formed due to the pressure applied on the foot during gait. This type of analysis can be done for different areas of the foot as well as for each individual and combination of biometrics.

Cross-correlation maps are created to quantify the heterogeneity/homogeneity of MI foot biometrics as a novel tool to analyze distributions of MI biometrics in the foot. This analysis can be used for more powerful indices development. For example, region specific perfusion may be critical for better pre-ulcer detection due to pressure/callus formation. Or it may be critical when looking at vascular reactivity after an intervention in correlation to known angiosomes. A correlation between region-wise limb perfusion and ABI values is possible with the present system, overcoming the issue that there is no literature describing how a low ABI affects spatial distribution of perfusion to angiosomes in the foot.

Figure 20:
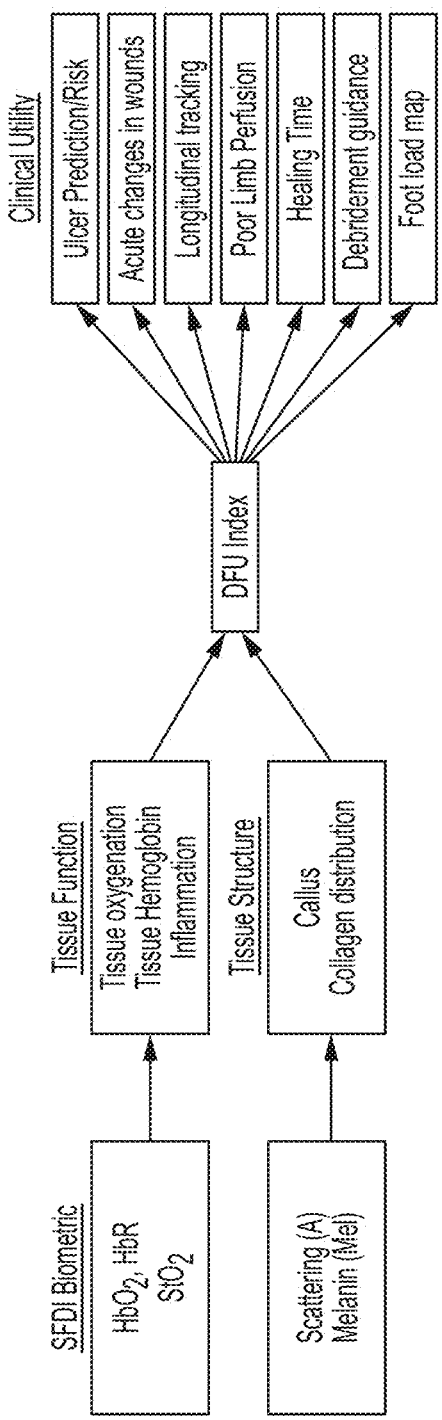
FIG. 20 illustrates building of an informative index based on embodiments of the present disclosure.

FIG. 20 illustrates building of an informative index based on embodiments of the present disclosure. A DFU index is developed based on MI-DFU biometrics that informs a clinician of a clinical outcome.

Figure 21:
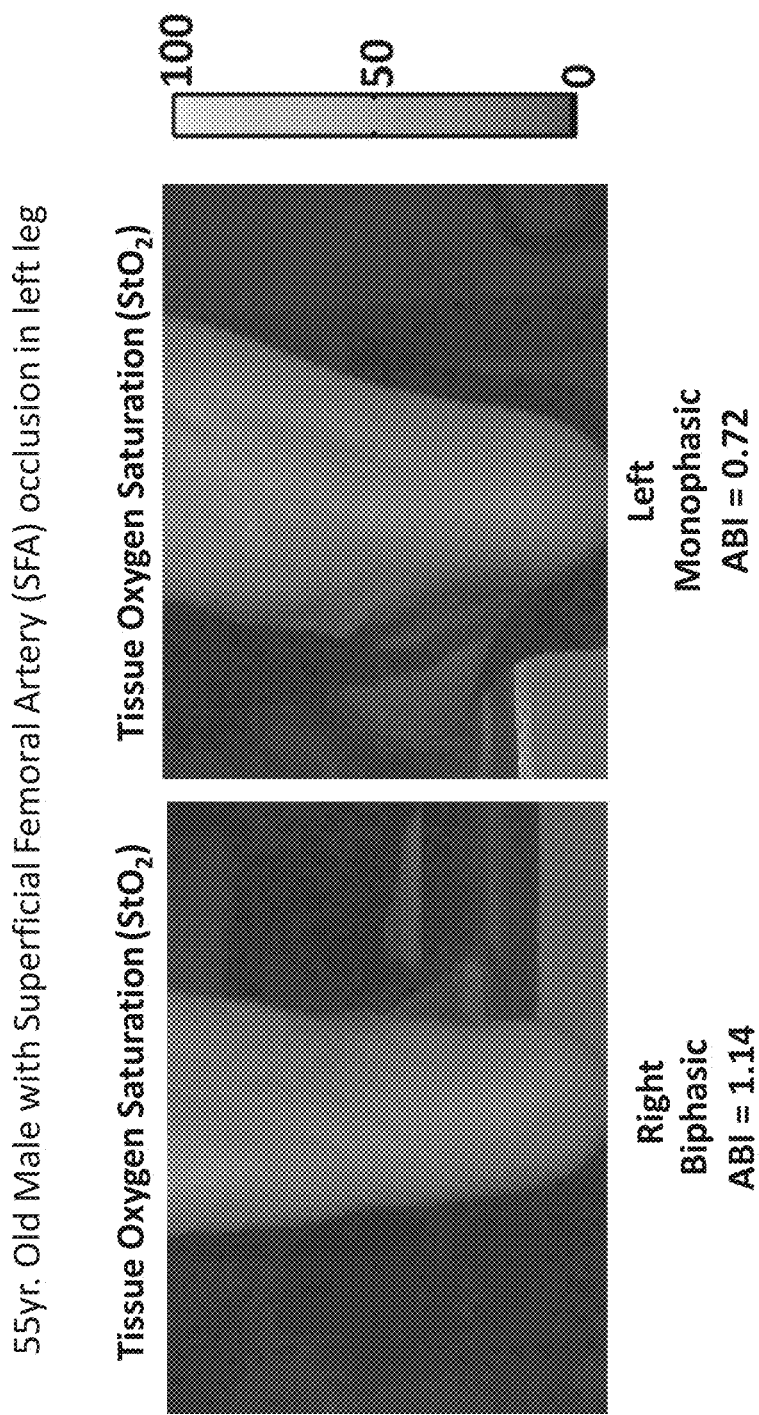
FIG. 21 illustrates images of vascular disease according to embodiments of the present disclosure.
Figure 22:
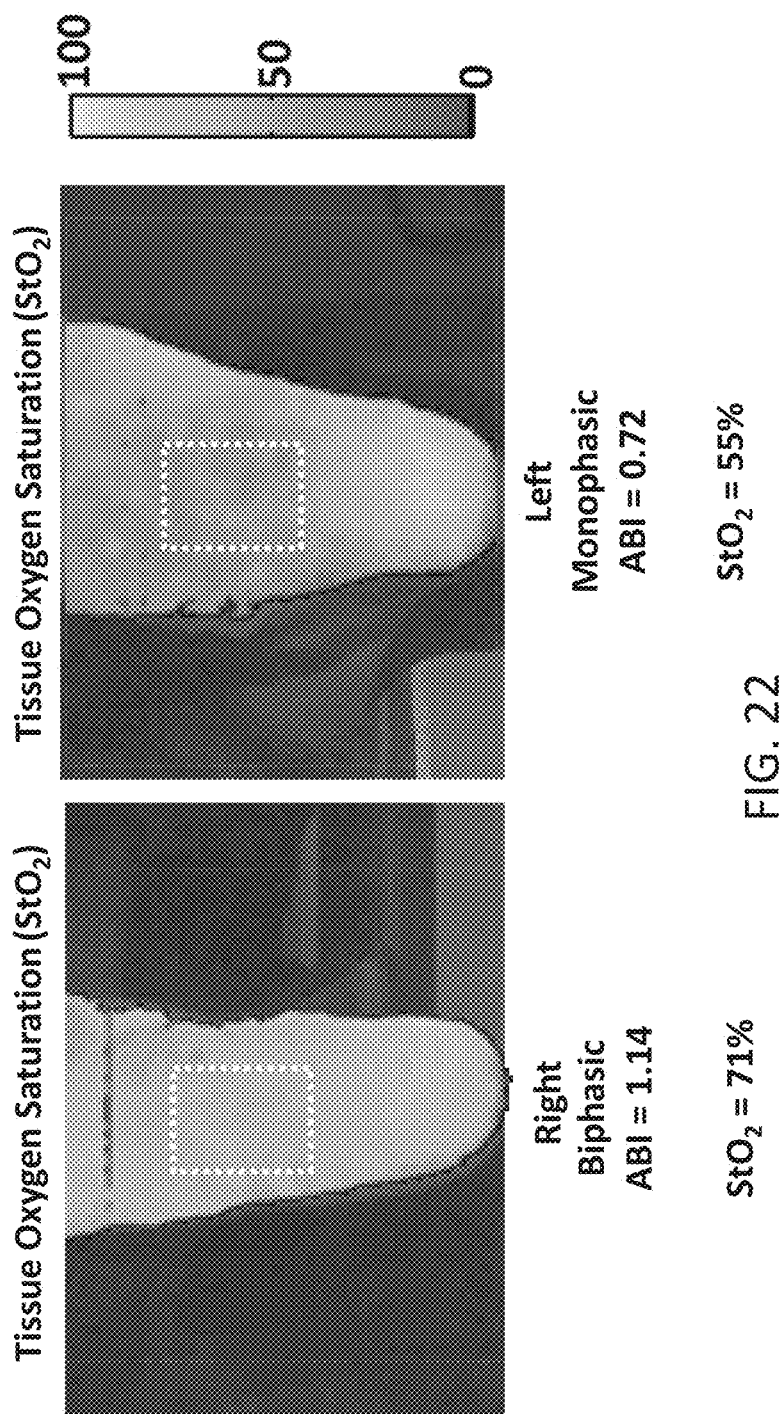
FIG. 22 illustrates images of vascular disease according to embodiments of the present disclosure.

FIGS. 21 and 22 illustrate images of vascular disease according to embodiments of the present disclosure. The present system is able to identify spatial features of the physiology which correspond to the location of angiosomes. FIGS. 21 and 22 show region-wise estimates of tissue oxygen saturation. Moreover, this has been correlated with ankle-brachial index (ABI) and digital waveform analysis for this subject. While the right foot in the figures has a biphasic waveform and an ABI of 1.14 and shows good oxygenation in the arch of the foot, the left foot in the figures has a monophasic waveform and an ABI of 0.72 and shows comparatively poor oxygenation in the arch of the foot compared to the heel region.

Figure 23:
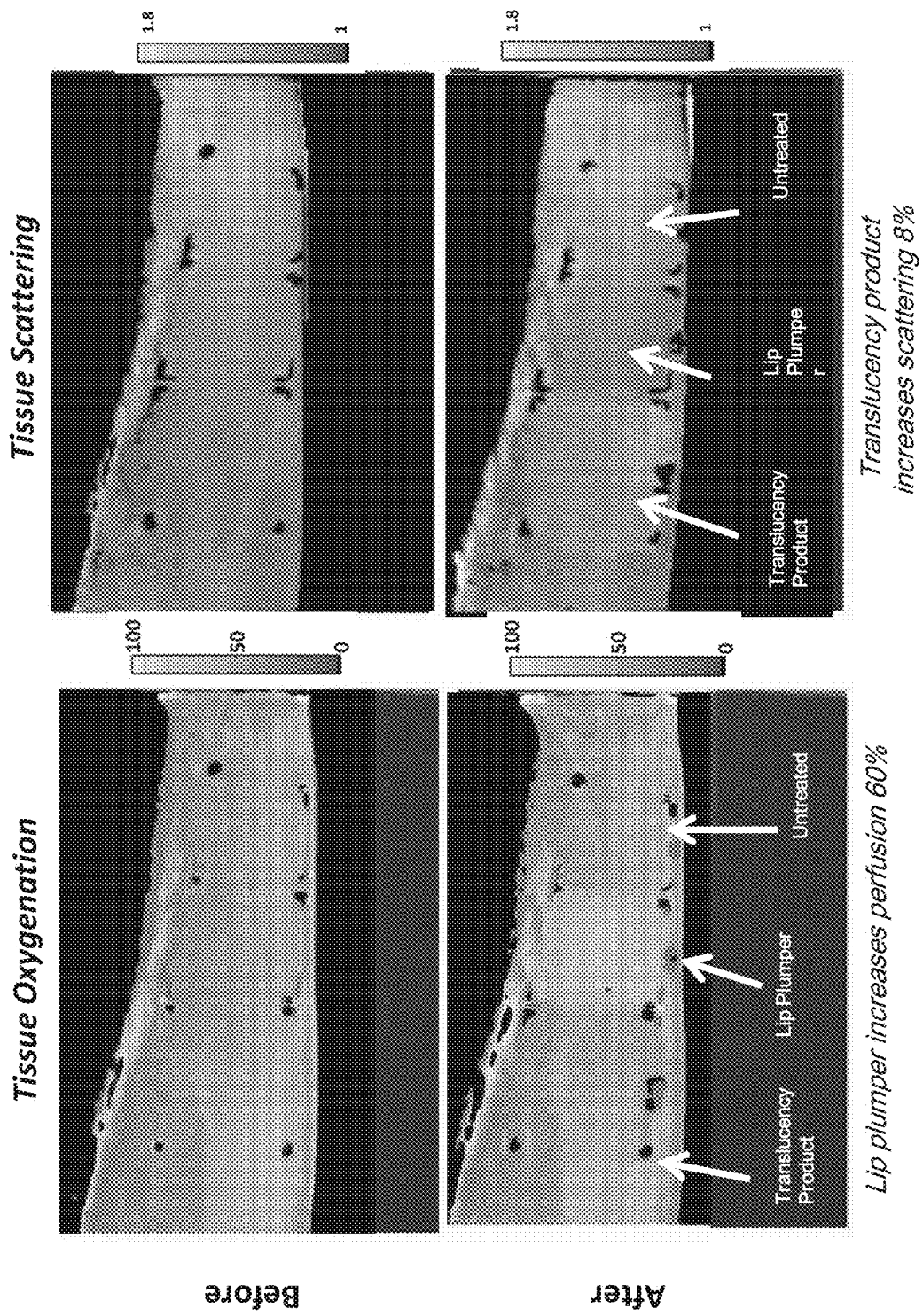
FIG. 23 illustrates imaging of effects of superficial topical products according to embodiments of the present disclosure.
Figure 24:
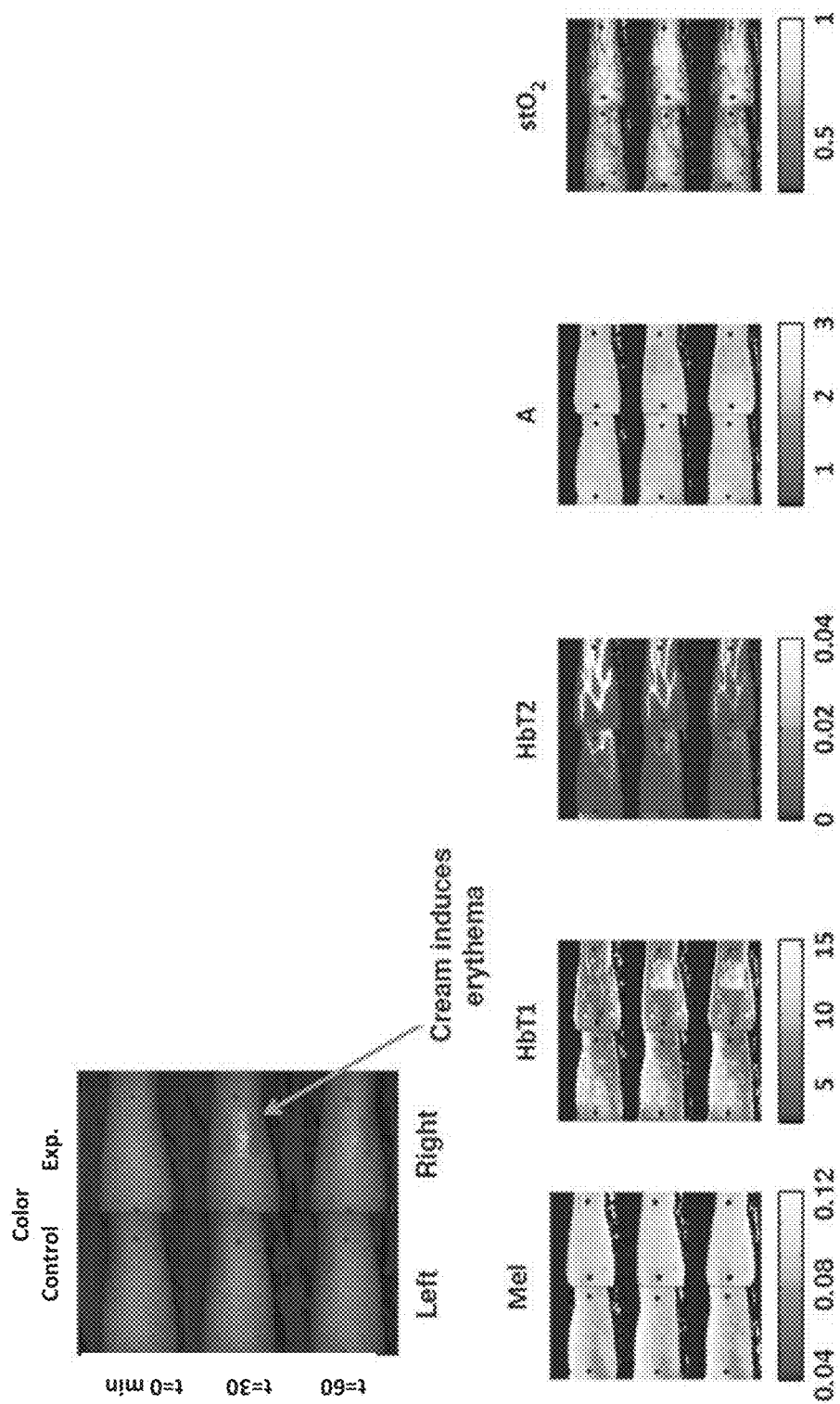
FIG. 24 illustrates imaging of effects of superficial topical products according to embodiments of the present disclosure.

FIGS. 23 and 24 illustrate imaging of effects of superficial topical products according to embodiments of the present disclosure. The unique, depth-dependent signatures resulting from the present system inform on small- and large-vessel disease by reporting superficial (roughly millimeter or sub-millimeter depths) and deep-tissue (roughly 1 mm or deeper) hemoglobin concentration (i.e. blood volume) measures, respectively. FIGS. 23 and 24 show the effects of a topical "lip plumper" agent designed to create an inflammatory response in the superficial skin (i.e. papillary dermis). FIG. 24 shows that changes/alterations in the superficial contrast from the induced blood perfusion can be isolated from the deeper structures (i.e. veins) which do not show the induced contrast.

FIGS. 25A, 25B, 25C, 25D, 25E and 25F illustrate imaging effects of deep vascular changes and modifications from laser therapy according to embodiments of the present disclosure. FIGS. 25A, 25B, 25C, 25D, 25E and 25F show the effects of pulsed laser therapy, which acutely after treatment creates a large pooling of blood in the deeper skin structures (reticular dermis and sub-cutis).

Figure 26:
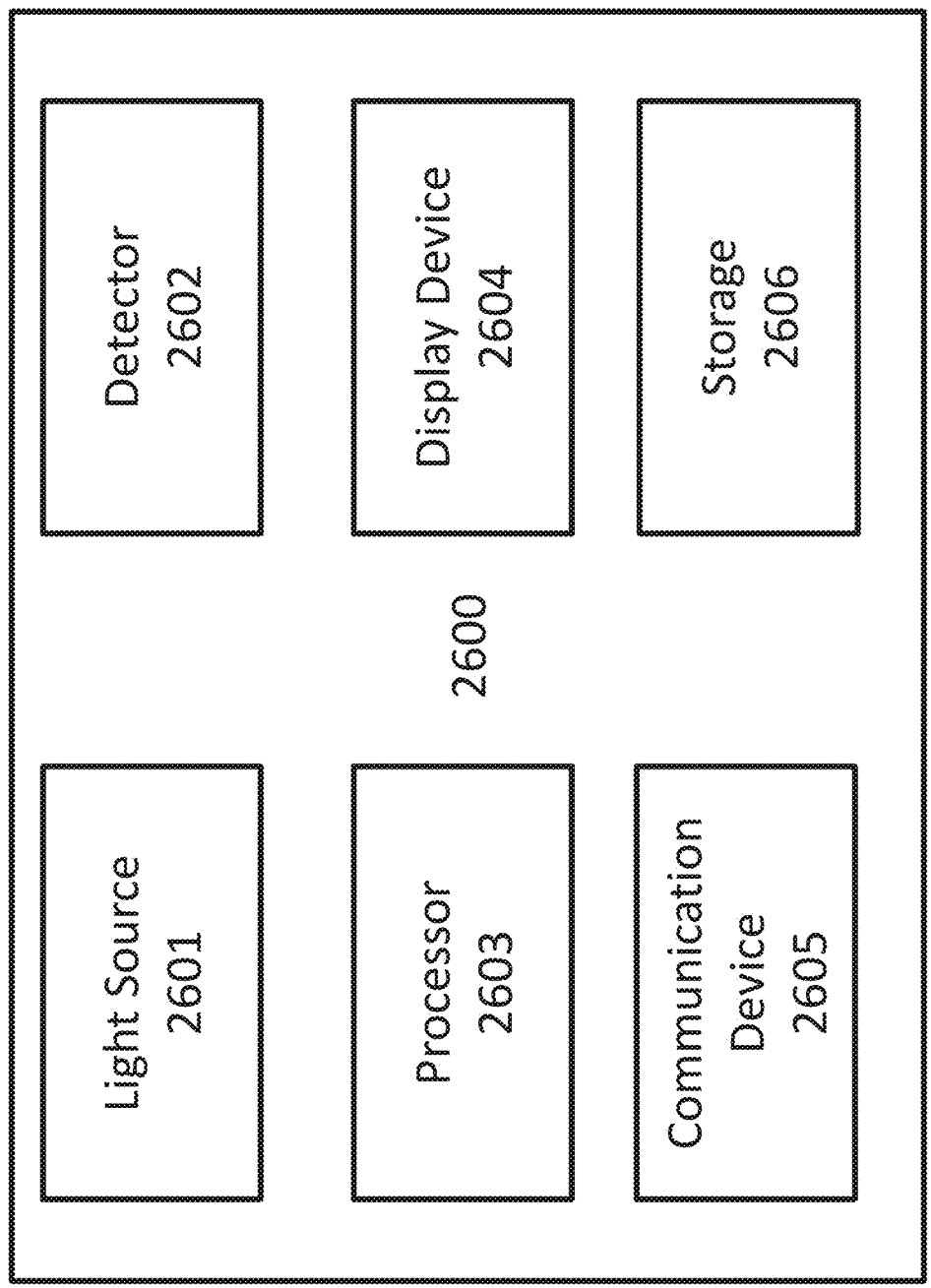
FIG. 26 illustrates an exemplary optical measurement system for use with embodiments of the present disclosure.

FIG. 26 illustrates an exemplary optical measurement system for use with embodiments of the present disclosure. An exemplary optical measurement system 2600 includes a light source 2601 with one or more wavelengths. The light source 2601 is configured to illuminate an area of tissue. The system 2600 includes a detector 2602 configured to capture the light reflecting from the tissue at the one or more illumination wavelengths. The system 2600 includes a processor 2603 configured to compute, based on the detected signal, one or more estimates of tissue vascular health. The system 2600 further includes a display device 2604 configured to display the tissue vascular reactivity or other data. The system 2600 further includes a communication device 2605 (e.g. electronic data transfer) configured to report the tissue vascular reactivity or other data. The system 2600 further includes storage 2606 configured to store the tissue vascular reactivity or other data.

Processor 2603 is configured to separately characterize multiple tissue compartments or regions, based on spatially distinct areas identified in the processed image data. These spatially distinct areas can be lateral changes, such as identifying and/or quantifying regions of high or low perfusion within the image plane, or they can be depth-dependent changes, such as the ability to resolve and quantify pigmentation (~100 μm depths), superficial capillaries (100 μm-1500 μm depths) and deeper blood signatures (1500 μm and deeper), or the ability to quantify the thickness of a callus layer (absorption contrast). Discussions regarding such capabilities are provided above with regard to FIGS. 9, 10A and 10B, where a 3-layer tissue geometry is used to represent and analyze the observed reflectance data using spatial frequency and wavelength contrast. The resulting metrics (absorption, scattering, chromophore concentration, etc) can then be used individually or in combination, such as, e.g., an index, as described above in regards to FIGS. 6A, 6B, 14A, 14B and 20, to provide estimates of tissue health and/or vascular reactivity.

Processor 2603 is configured to execute instructions stored in storage 2606, where execution of the instructions by the processor 2603 causes the system 2600 to compute various estimates and other data and analyses described herein. Storage 2606 can be any computer readable medium, including non-transitory computer readable medium.

The system 2600 reports an estimate of tissue vascular health, which may include one or more estimates of tissue health and/or risk of tissue injury, based on the concentration, lateral distribution, and/or depth distribution of one or more subsurface tissue constituents exhibiting optical absorption and/or scattering contrast (e.g. blood concentration, blood oxygenation, water/hydration, collagen, lipids, exogenous agents), and/or based on an estimate of vasomotor regulation or vascular reactivity derived from the one or more tissue constituents exhibiting absorption and/or scattering contrast.

The detector 2602 can be configured to provide a single time point capture. The detector 2602 can be a 2D imaging detector array. The 2D imaging detector array may comprise a CCD/CMOS camera. The detector 2602 can be a single-element detector. The single-element detector can be one of a photodiode and an optical fiber relay to a detection system. The detector 2602 can include multiple single-element detectors configured to collect reflected light from multiple tissue locations.

The source 2601 can be configured to create at least one spatially-structure light pattern over the tissue surface. The spatially-structured light is configured to perform spatial frequency domain imaging.

The display 2604 can be one of an interactive touchscreen device, a tablet, and a digital phone. The optical measurement system 2600 can be configured to interface with a computer system, tablet, or digital phone with a wired or wireless connection.

Figure 27B:
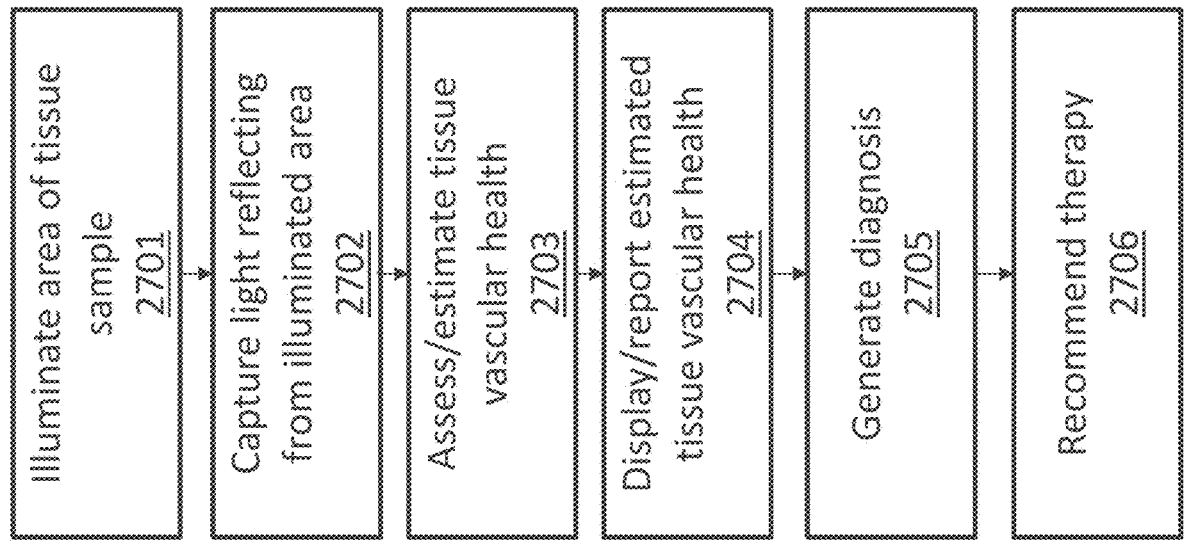
FIGS. 27A and 27B illustrate an exemplary method for estimating tissue vascular health according to embodiments of the present disclosure.
Figure 27A:
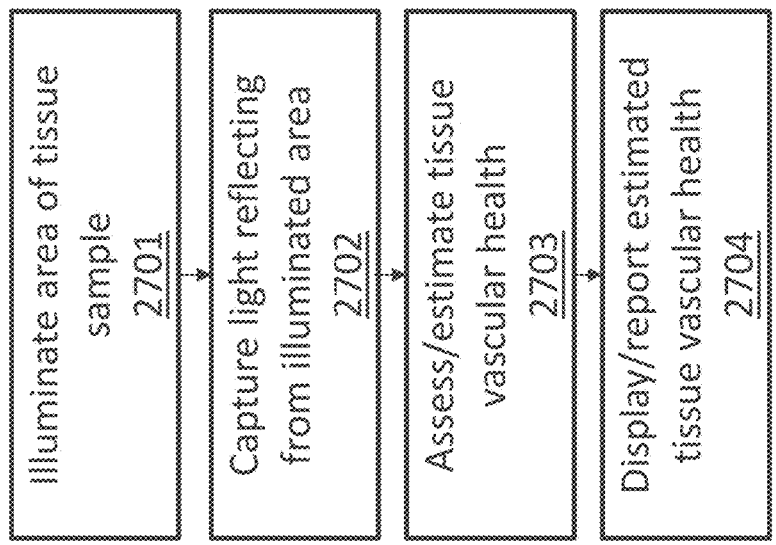

FIG. 27A illustrates an exemplary method for estimating tissue vascular health according to embodiments of the present disclosure. An area of a tissue sample is illuminated 2701, light reflecting from the illuminated area is captured 2702. The light can be captured by a detector configured to capture light reflecting from the tissue at one or more illumination wavelengths. The tissue vascular health or vascular reactivity is assessed and/or estimated 2703 based on the detected or captured light signals, and then displayed and/or otherwise reported 2704.

The estimate of tissue vascular health may include one or more estimates of tissue health and/or risk of tissue injury, based on the concentration, lateral distribution, and/or depth distribution of one or more subsurface tissue constituents exhibiting optical absorption and/or scattering contrast (e.g., blood concentration, blood oxygenation, water/hydration, collagen, lipids, exogenous agents), and/or based on an estimate of vasomotor regulation or vascular reactivity derived from the one or more tissue constituents exhibiting absorption and/or scattering contrast.

As shown in FIG. 27B, a diagnosis of tissue health and/or risk may be generated 2705 from the estimated tissue vascular reactivity of the illuminated area of tissue. This diagnosis may be made either by the practicing clinician or the device itself. A therapy, treatment, treatment product, or a behavioral change may be recommended 2706 in response to the diagnosis. Again, this recommendation may be made either by the practicing clinician or the device itself.

Illuminating the tissue sample 2701 can include illuminating the tissue sample with a spatially-structured light pattern over the tissue surface. The spatially-structured light pattern can be configured to perform spatial frequency domain imaging.

The tissue vascular reactivity of the tissue sample can be assessed 2703 in two ways. In one way, dynamic changes can be measured to probe reactivity directly, such as during a vascular cuff occlusion. In another way, single time point measures are generated, such as blood pooling and capillary perfusion indices, which individually or in combination can be used as an analog/correlate to vascular reactivity. In this way, a method for a simpler and faster clinical examination of vascular health is provided.

In an example of the workflow of the exemplary method shown in FIGS. 27A and 27B, an SFDI dataset would be acquired via illumination (at 2701) and detection (at 2702) of structured and non structured illumination using both visible and near-infrared wavelengths. The analysis may proceed as depicted in and discussed with regard to FIGS. 4A, 4B, 4C and 4D, where some of the wavelengths have structured illumination, and then this process is repeated at one or more wavelengths to compute chromophore information from the absorption coefficient (blood in a specific layer, StO2, H2O, and/or etc). In one particular embodiment, the processor (at 2603) may instead compute chromophores directly based on the multi-spectral dataset. Such chromophore information is depicted in and discussed with regards to FIGS. 5A, 5B, 6A, 6B or 13. Based on these data, one or more assessments of vascular health may be computed (at 2703). A specific example is described with regards to FIGS. 14A and 14B, where an ulcer risk index is derived from a ratio of superficial and deep hemoglobin signatures. Based on this information, a display and/or report of this information is provided (at 2704), such as is depicted in and described with regards to FIGS. 14A and 14B. This information can then be used to inform a diagnosis (at 2705), such as an assessment that the patient has poor vascular health (e.g. high risk of ulceration). This diagnosis may be made either by the practicing clinician or the device itself. Subsequently, a therapy recommendation may be made (at 2706), such as a more frequent patient monitoring protocol, a recommendation for offloading or footwear, a referral to a specialist, or a recommendation for a medical procedure such as arterial stenting. Again, this recommendation may be made either by the practicing clinician or the device itself.

All features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Express recitation of every possible combination and substitution is overly burdensome, especially given that the permissibility of each and every such combination and substitution will be readily recognized by those of ordinary skill in the art upon reading this description.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic intervening) entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed:

1. A method to estimate tissue vascular health of a tissue sample, comprising:

illuminating an area of the tissue sample with a spatially-structured light pattern extending over the entire tissue surface of the illuminated area of the tissue sample at a plurality of wavelengths;

simultaneously capturing light signals reflecting from a first skin layer within the illuminated area of the tissue sample and separately reflecting from a second skin layer within the illuminated area of the tissue sample by a detector configured to capture light signals reflecting from the first skin layer within the illuminated area of the tissue sample and separately reflecting from the second skin layer within the illuminated area of the tissue sample at the plurality of illumination wavelengths;

determining layer specific chromophore information for the first skin layer within the illuminated area of the tissue sample from the captured light signals comprising light signals reflected from the first skin layer within the illuminated area of the tissue sample and separately determining layer specific chromophore information for the second skin layer within the illuminated area of the tissue sample from the captured light signals comprising light signals reflected from the second skin layer within the illuminated area of the tissue sample, wherein the steps of determining the layer specific chromophore information for the first skin layer from the captured light signals comprising light signals reflected from the first skin layer and determining layer specific chromophore information for the second skin layer from the captured light signals comprising light signals reflected from the second skin layer includes discriminating contrast elements from the captured light signals to resolve layer specific chromophore information, wherein the captured light signals comprising varying spatial frequency and wavelength content, and estimating tissue vascular health of the illuminated area of the tissue sample as a function of the layer specific chromophore information of the first and second skin layers within the illuminated area of the tissue sample.

2. The method of claim 1 further comprising reporting or displaying the estimated tissue vascular health of the illuminated area of tissue.

3. The method of claim 2 further comprising generating a diagnosis of tissue health and/or risk from the estimated tissue vascular reactivity of the illuminated area of tissue.

4. The method of claim 3 further comprising recommending a therapy, treatment, a treatment product, or a behavioral change in response to the diagnosis.

5. The method of claim 1 wherein the layer specific chromophore information is a layer specific hemoglobin signature.

6. The method of claim 5 wherein the estimate of tissue vascular health is derived from a ratio of the hemoglobin signature of the first layer to the hemoglobin signature of the second layer.

* * * * *